United States Patent
Benn et al.

(10) Patent No.: US 9,642,783 B2
(45) Date of Patent: *May 9, 2017

(54) DEPILATORY COMPOSITIONS

(71) Applicant: L'OREAL, Paris (FR)

(72) Inventors: Mark Benn, Union, NJ (US); Michael Degeorge, Old Bridge, NJ (US)

(73) Assignee: L'OREAL, Paris (FR)

( * ) Notice: Subject to any disclaimer, the term of this patent is extended or adjusted under 35 U.S.C. 154(b) by 120 days.

This patent is subject to a terminal disclaimer.

(21) Appl. No.: 14/243,522

(22) Filed: Apr. 2, 2014

(65) Prior Publication Data

US 2015/0283042 A1  Oct. 8, 2015

(51) Int. Cl.
| | |
|---|---|
| *A61K 8/64* | (2006.01) |
| *A61K 8/02* | (2006.01) |
| *A61K 8/19* | (2006.01) |
| *A61K 8/26* | (2006.01) |
| *A61K 8/29* | (2006.01) |
| *A61K 8/37* | (2006.01) |
| *A61K 8/41* | (2006.01) |
| *A61K 8/43* | (2006.01) |
| *A61K 8/46* | (2006.01) |
| *A61K 8/49* | (2006.01) |
| *A61K 8/73* | (2006.01) |
| *A61K 8/81* | (2006.01) |
| *A61K 8/86* | (2006.01) |
| *A61K 8/92* | (2006.01) |
| *A61Q 5/04* | (2006.01) |
| *A61Q 9/04* | (2006.01) |
| *A61K 8/25* | (2006.01) |
| *A61K 8/31* | (2006.01) |
| *A61K 8/44* | (2006.01) |
| *A61K 8/58* | (2006.01) |
| *A61K 8/97* | (2017.01) |

(52) U.S. Cl.
CPC ............... *A61K 8/022* (2013.01); *A61K 8/19* (2013.01); *A61K 8/25* (2013.01); *A61K 8/26* (2013.01); *A61K 8/29* (2013.01); *A61K 8/31* (2013.01); *A61K 8/375* (2013.01); *A61K 8/41* (2013.01); *A61K 8/43* (2013.01); *A61K 8/44* (2013.01); *A61K 8/46* (2013.01); *A61K 8/463* (2013.01); *A61K 8/4973* (2013.01); *A61K 8/585* (2013.01); *A61K 8/732* (2013.01); *A61K 8/8152* (2013.01); *A61K 8/86* (2013.01); *A61K 8/92* (2013.01); *A61K 8/97* (2013.01); *A61Q 5/04* (2013.01); *A61Q 9/04* (2013.01); *A61K 2800/31* (2013.01); *A61K 2800/5922* (2013.01); *A61K 2800/882* (2013.01); *A61K 2800/884* (2013.01)

(58) Field of Classification Search
CPC ... A61K 8/43; A61K 8/19; A61K 8/42; A61K 2800/884; A61K 8/25; A61K 8/41; A61K 8/365; A61K 8/415; A61K 8/36; A61K 8/463; A61K 8/4926; A61K 8/73; A61K 8/22; A61K 8/26; A61K 8/494; A61K 8/4953; A61K 8/97; A61Q 8/10; A61Q 5/02; A61Q 17/04; A61Q 19/00; A61Q 19/08; A61Q 5/065; A61Q 11/00; A61Q 17/005; A61Q 19/10; A61Q 1/02; A61Q 1/06; A61Q 3/00; A61Q 5/08; A61Q 90/02; A61Q 1/10; A61Q 5/004

See application file for complete search history.

(56) References Cited

U.S. PATENT DOCUMENTS

| | | | |
|---|---|---|---|
| 3,154,470 A | 10/1964 | Braun et al. | |
| 3,194,736 A | 7/1965 | Braun et al. | |
| 3,533,417 A | 10/1970 | Bartoszewicz | |
| 7,470,725 B2 | 12/2008 | Schwertfeger et al. | |
| 2002/0146380 A1* | 10/2002 | Nambu ................... | A61K 8/46 424/70.16 |
| 2005/0192366 A1 | 9/2005 | Ou et al. | |
| 2008/0138304 A1 | 6/2008 | Biggs et al. | |
| 2012/0052035 A1* | 3/2012 | Ciemnolonski ........ | A61K 8/042 424/70.11 |
| 2012/0308621 A1 | 12/2012 | Novejarque Conde | |
| 2013/0202544 A1 | 8/2013 | Foltis et al. | |
| 2013/0205514 A1 | 8/2013 | Evison et al. | |

FOREIGN PATENT DOCUMENTS

| | | | | |
|---|---|---|---|---|
| DE | 33 38 957 A1 | 5/1985 | | |
| EP | 1 902 752 A1 | 3/2008 | | |
| FR | 2 883 169 A1 | 9/2006 | | |
| FR | 2883169 A1 * | 9/2006 | ............... | A61K 8/19 |
| GB | 824429 | 12/1959 | | |
| GB | 2496447 A | 5/2013 | | |
| JP | 2000026251 A | 1/2000 | | |
| JP | 2002 293723 A | 10/2002 | | |

(Continued)

OTHER PUBLICATIONS

U.S. Appl. No. 14/243,466, filed Apr. 2, 2014, Degeorge et al.
U.S. Appl. No. 14/243,494, filed Apr. 2, 2014, Degeorge et al.
U.S. Appl. No. 14/2143,522, filed Apr. 2, 2014, Benn et al.
Goddard, Ed et al., Polysaccharides (Sugars, Gums) Used in Cosmetics, Principles of polymer science and technology in cosmetics and personal care, Dec. 13, 2013, p. 325-389, Dekker M., New York.
Technical Services Branch for the USDA National Organic Program, Dextrin Handling/Processing, Technical Evaluation Report, Oct. 12, 2011.

(Continued)

*Primary Examiner* — Nannette Holloman
(74) *Attorney, Agent, or Firm* — Polsinelli PC

(57) ABSTRACT

Disclosed herein is a powder composition containing an alkaline material comprising hydroxide-containing compounds, two carbonate compounds, a starch, a silica material, a liquid fatty substance, an acrylic polymer, a sulfur-containing compound, and a chelant compound. When the powder composition is mixed with an aqueous composition, a ready to use composition for removing or depilating hair is formed.

32 Claims, No Drawings

(56) References Cited

FOREIGN PATENT DOCUMENTS

| WO | WO 2005/123022 A | 12/2005 |
|----|------------------|---------|
| WO | WO-2007/080411 A1 | 7/2007 |
| WO | 2007126410 A2 | 11/2007 |
| WO | WO-2012/047957 A1 | 4/2012 |
| WO | 2013076238 A1 | 5/2013 |
| WO | WO-2014/020352 A1 | 2/2014 |

OTHER PUBLICATIONS

Brunauer, Stephen, Emmett, P.H., Teller, Edward, Adsorption of Gases in Multimolecular Layers, Journal of American Chemist Society, vol. 60, Feb. 1938, pp. 309-319.
Notification Concerning Transmittal of International Preliminary Report on Patentability (Chapter I of the Patent Cooperation Treaty), mailed Oct. 13, 2016.

* cited by examiner

DEPILATORY COMPOSITIONS

FIELD OF THE INVENTION

The present application relates to depilatory compositions for use on keratinous substrates. In particular, it relates to powder compositions and methods for hair removal or hair degradation.

BACKGROUND OF THE INVENTION

Cosmetic and personal care products for use on keratinous substrates such as skin and hair are available commercially in various forms, for example, as creams, lotions, gels, pastes, and powders. Regardless of the form, these products have to achieve and provide certain benefits and attributes such as efficaciousness, cosmeticity, desirable texture, stable formulations, and ease and convenience of use and application. Moreover, changing market needs present an opportunity to produce cosmetic and personal care products that are readily available and easy and convenient for the consumer to use, store, and travel with, as well as provide cost savings to the manufacturer in terms of processing, storage space and transport.

Thus, products that are commercially available in powder form have the advantage of ease of transportability, packaging, and storage. However, products in powder form may require a wetting or mixing step with water in order to form ready to use compositions immediately prior to use. Thus, aside from the formulation challenge of providing a stable powder composition that is easy to mix or disperse in an aqueous composition, the powder composition must be formulated in such a way that the resulting ready to use compositions have a texture and viscosity such that it is easy to apply onto surface and does not drip or run. If the powder composition contains active agents or ingredients that are designed to provide a particular effect on the treated surface, it is also desirable that the efficacy of such ingredients be preserved in the powder composition and in the ready to use compositions.

One such product that may be available in powder form but which is generally contacted with water or an aqueous composition prior to use is a depilatory composition. Depilatory compositions are employed for removing superfluous body hair and include a compound, such as a compound containing a thiol group, that degrades hair keratin or that aids in removing hair.

According to the present invention there is provided a depilatory composition in the form of a powder comprising an alkaline material comprising a hydroxide-containing compound, at least two carbonate compounds, a sulfur-containing compound, a silica material, a liquid fatty substance, an acrylic polymer, wax, and a chelant compound. The powder composition of the invention is capable of being contacted or mixed with an aqueous composition in order to form a ready to use composition having a depilatory effect when applied onto a keratinous substrate such as skin with hair or hair. The ready to use composition is formed either in situ on the keratinous substrate or in a vessel prior to application onto the substrate.

BRIEF SUMMARY OF THE INVENTION

The present invention relates to a powder composition containing,
(a) from about 1% to about 30% by weight of active material of at least one alkaline material comprising at least one hydroxide-containing compound selected from alkali metal hydroxides, alkaline-earth metal hydroxides, transition metal hydroxides, and mixtures thereof;
(b) from about 20% to about 40% by weight of at least two carbonate compounds selected from calcium carbonate, lithium carbonate, sodium carbonate, potassium carbonate, guanidine carbonate, and mixtures thereof;
(c) from about 1% to about 25% by weight of at least one starch material;
(d) from about 0.1% to about 20% by weight of at least one silica material;
(e) from about 5% to about 50% by weight of at least one liquid fatty substance;
(f) from about 0.5% to about 15% by weight of at least one acrylic polymer;
(g) from about 5% to about 20% by weight of at least one sulfur-containing compound; and
(h) from about 0.5% to about 5% by weight of at least one chelant compound;
all weights above being based on the total weight of the powder composition.

The above-described powder composition is capable of being mixed or contacted with an aqueous composition containing a cosmetically acceptable solvent selected from water and a water/organic solvent mixture either in situ on a keratinous substrate to be treated or in order to form a ready to use composition for application onto a keratinous substrate such as skin with hair and hair.

Thus, the present invention also relates to a ready to use composition comprising the above-described powder composition and an aqueous composition containing a cosmetically acceptable solvent selected from water and a water/organic solvent mixture; wherein the aqueous composition may additionally contain at least one chelant compound; wherein the ready to use composition is formed when the powder composition is mixed or contacted with the aqueous composition in a weight ratio of the powder composition to the aqueous composition of from about 1:3 to about 1:10; wherein the pH of the ready to use composition ranges from about 9 to about 14; and wherein the viscosity of the ready to use composition is from about 30 uD to about 100 uD.

The invention also relates to a method of depilating or degrading hair, the method comprising the steps of: 1) mixing the above described powder composition with the above-described aqueous composition in a weight ratio of from about 1:3 to about 1:10 in order to form a ready to use composition, wherein the pH of the ready to use composition ranges from about 9 to about 14; and wherein the viscosity of the ready to use composition is from about 30 uD to about 100 uD; and 2) contacting hair with the ready to use composition for a sufficient period of time to remove or degrade the hair.

The aqueous composition may additionally contain at least one chelant compound.

The powder composition and/or the aqueous composition optionally includes other components appropriate for the intended end use of the powder and aqueous compositions, such as for example, non-starch, non-acrylic polymers, clay, surfactants, organic amines, carbonate compounds, emulsifying agents, pigments, conditioning agents, fragrances, and preservatives.

In certain embodiments, the ready to use composition formed from mixing the powder composition and the aqueous composition of the present invention is left to stand on the hair for a period of time ranging from about 5 to 60 minutes, and preferably, from 5 to 30 minutes, after which, the hair is rinsed and optionally, dried.

In some embodiments, the powder composition and the aqueous composition of the present invention are contained in separate compartments which comprise a multi-compartment kit. When hair is to be straightened or relaxed, the powder composition and the aqueous composition in the kit are mixed together in order to form a ready to use composition that is then applied onto hair.

In other embodiments, the powder composition is provided to the end user in a container such as a paper or plastic envelope, or a bottle, or a tube.

In preferred embodiments, the powder composition is essentially free of water.

In particular embodiments, the aqueous composition comprises 100% water.

In other embodiments, the powder composition of the present invention may be mixed with varying amounts of the aqueous composition of the present invention to form ready to use compositions to suit different types of hair and/or to achieve different degrees of hair relaxation or straightening.

The compositions of the present invention are stable over time due to minimal moisture content; they can be stored for several months without modification.

The powder composition of the present invention may also be characterized as a free flowing powder that is easy to handle, easily pourable, has non-sticky and non-clinging properties, and does not exhibit visible clumping of powder particles. Thus, the powder composition of the invention may be comprised of unagglomerated, discrete particles.

The powder composition remains free flowing after packaging and storage.

It is to be understood that both the foregoing general description and the following detailed description are exemplary and explanatory only, and are not restrictive of the invention.

DETAILED DESCRIPTION OF THE INVENTION

As used herein, the expression "at least one" means one or more and thus includes individual components as well as mixtures/combinations.

Other than in the operating examples, or where otherwise indicated, all numbers expressing quantities of ingredients and/or reaction conditions are to be understood as being modified in all instances by the term "about," meaning within 5% to 10% of the indicated number.

The term "aqueous composition" means that the composition comprises water and optionally, substances of a formulation which, due to their hydrophilic character, can be mixed and/or dissolved and/or dispersed in water.

"Keratinous substrates" as used herein, include, but are not limited to skin, lips, and keratinous fibers such as hair and eyelashes.

"Wax" as used herein means a hydrocarbon material, natural or synthetic, and having a melting point in the ranges disclosed below. Polymers and copolymers are included in this definition. Wax as used herein may also include a material composed of several components, including wax esters such as those derived from carboxylic acids and fatty alcohols, wax alcohols, and hydrocarbons.

The term "essentially free of water" as used herein means "no free water." "No free water" herein means that water is not added as a separate component by itself during the process of making the powder composition of the invention. "Free water" as used herein does not include the water that may be present as a component in a raw material or ingredient that is added during the process of making the powder composition of the invention.

"Volatile", as used herein, means having a flash point of less than about 100° C.

"Non-volatile", as used herein, means having a flash point of greater than about 100° C.

"Depilatory" and all variations of the term as used herein means removal or degradation of hair, e.g, body hair.

The compositions and methods of the present invention can comprise, consist of, or consist essentially of the essential elements and limitations of the invention described herein, as well as any additional or optional ingredients, components, or limitations described herein or otherwise useful.

In an embodiment, the present invention relates to a powder composition comprising:
  (a) from about 1% to about 20% by weight of active material of at least one alkaline material comprising at least one hydroxide-containing compound selected from alkali metal hydroxides, alkaline-earth metal hydroxides, transition metal hydroxides, and mixtures thereof;
  (b) from about 20% to about 40% by weight of at least two carbonate compounds selected from calcium carbonate, lithium carbonate, sodium carbonate, potassium carbonate, guanidine carbonate, and mixtures thereof;
  (c) from about 1% to about 12% by weight of at least one starch material;
  (d) from about 0.1% to about 5% by weight of at least one silica material;
  (e) from about 5% to about 40% by weight of at least one liquid fatty substance;
  (f) from about 0.5% to about 5% by weight of at least one acrylic polymer;
  (g) from about 5% to about 20% by weight of at least one sulfur-containing compound; and
  (h) from about 0.5% to about 5% by weight of at least one chelant compound;
all weights above being based on the total weight of the powder composition.

The above-described powder composition is capable of being mixed with an aqueous composition comprising a cosmetically acceptable solvent selected from water and a water/organic solvent mixture in order to form a ready to use composition.

In one embodiment, the present invention relates to a ready to use composition for relaxing or straightening hair comprising:
A. a powder composition containing:
  (a) from about 1% to about 30% by weight of at least one alkaline material comprising at least one hydroxide-containing compound selected from alkali metal hydroxides, alkaline-earth metal hydroxides, transition metal hydroxides, and mixtures thereof;
  (b) from about 25% to about 35% by weight of at least two carbonate compounds selected from calcium carbonate, lithium carbonate, sodium carbonate, potassium carbonate, guanidine carbonate, and mixtures thereof;
  (c) from about 1% to about 25% by weight of at least one starch material;
  (d) from about 0.1% to about 20% by weight of at least one silica material;
  (e) from about 5% to about 50% by weight of at least one liquid fatty substance;
  (f) from about 0.5% to about 15% by weight of at least one acrylic polymer; and (g) from about 5% to about 20% by weight of at least one sulfur-containing compound;

all weights above being based on the total weight of the powder composition;

B. an aqueous composition containing a cosmetically acceptable solvent selected from water and a water/organic solvent mixture;

wherein the powder composition and/or the aqueous composition additionally contains at least one chelant compound;

wherein the weight ratio of the powder composition to the aqueous composition of from about 1:3 to about 1:10;

wherein the pH of the ready to use composition ranges from about 9 to about 14; and wherein the viscosity of the ready to use composition is from about 30 uD to about 100 uD.

In an embodiment, the hydroxide-containing compound is selected from sodium hydroxide, potassium hydroxide, lithium hydroxide, calcium hydroxide, and mixtures thereof.

In another embodiment, the hydroxide-containing compound is calcium hydroxide and the two carbonate compounds are calcium carbonate and guanidine carbonate.

In an embodiment, the starch is selected from corn starch, potato starch, dextrin, maltodextrin, and mixtures thereof.

In another embodiment, the starch is corn starch.

In another embodiment, the starch is maltodextrin.

In an embodiment, the silica material comprises silica particles selected from hydrated silica, hydrophobic silica aerogel particle, and mixtures thereof.

In an embodiment, the silica particles are comprised of hydrated silica. In another embodiment, the silica particles are comprised of silica silylate.

In another embodiment, the fatty substance is selected from $C_6$-$C_{16}$ alkanes, non-silicone oils of plant, mineral or synthetic origin, liquid fatty alcohols, liquid fatty acids and liquid esters of a fatty acid and/or of a fatty alcohol, or mixtures thereof.

In an embodiment, the acrylic polymer is a crosslinked acrylic polymer selected from sodium polyacrylate, carbomer, acrylates C10-30 alkyl acrylate crosspolymer, and mixtures thereof.

In another embodiment, the chelant compound is selected from ethylenediaminetetraacetic acid (EDTA), its salts, and mixtures thereof.

In some embodiments, the powder composition and/or the aqueous composition further comprise one or more of the following: waxes, non-starch, non-acrylic polymers, clay, surfactants, and mixtures thereof.

In another embodiment, the present invention relates to a powder composition comprising:
(a) from about 4% to about 8% by weight of active material of at least one alkaline material comprising at least one hydroxide-containing compound selected from calcium hydroxide;
(b) from about 25% to 30% by weight of calcium carbonate and from about 0.5% to about 2% by weight of guanidine carbonate;
(c) from about 3% to about 10% by weight of at least one starch selected from: (i) starches derived from a plant source selected from corn, potato, sweet potato, pea, barley, wheat, rice, oat, sago, tapioca and sorghum; (ii) hydrolyzed starches selected from dextrin and maltodextrin; (iii) modified starches; and mixtures thereof;
(d) from about 0.5% to about 2% by weight of at least one silica material comprising silica particles selected from hydrated silica, hydrophobic silica aerogel particle, and mixtures thereof;
(e) from about 6% to about 26% by weight of at least one liquid fatty substance comprising mineral oil;
(f) from about 1% to about 10% by weight of at least one acrylic polymer selected from sodium polyacrylate, carbomer, acrylates C10-30 alkyl acrylate cross polymer, and mixtures thereof;
(g) from about 10% to about 15% by weight of at least one sulfur-containing compound selected from calcium thioglycolate, potassium thioglycolate, ammonium thioglycolate, and mixtures thereof;
(h) from about 3% to about 8% by weight of at least one wax;
(i) from about 2% to about 5% by weight of non-starch, non-acrylic polymer selected from a polyvinylpyrrolidone, a polysaccharide, and mixtures thereof; and
(j) from about 1% to about 10% by weight of at least one clay;

all weights above being based on the total weight of the powder composition.

When the powder composition is mixed with an aqueous composition containing a cosmetically acceptable solvent selected from water and a water/organic solvent mixture, a ready to use composition is formed. Furthermore, the powder composition and/or the aqueous composition contains at least one chelant compound present in an amount of from about 0.5% to about 5% by weight, based on the total weight of the powder composition or the aqueous composition.

In another embodiment, the present invention relates to a method of depilating hair, the method comprising the steps of:

1) mixing a powder composition with an aqueous composition in a weight ratio of from about 1:3 to about 1:10 in order to form a ready to use composition wherein the powder composition contains:
(a) from about 1% to about 30% by weight of active material of at least one alkaline material comprising at least one hydroxide-containing compound selected from alkali metal hydroxides, alkaline-earth metal hydroxides, transition metal hydroxides, and mixtures thereof;
(b) from about 20% to about 40% by weight of at least two carbonate compounds selected from calcium carbonate, lithium carbonate, sodium carbonate, potassium carbonate, guanidine carbonate, and mixtures thereof;
(c) from about 1% to about 25% by weight of at least one starch material;
(d) from about 0.1% to about 20% by weight of at least one silica material;
(e) from about 5% to about 50% by weight of at least one liquid fatty substance;
(f) from about 0.5% to about 5% by weight of at least one acrylic polymer; and
(g) from about 5% to about 20% by weight of at least one sulfur-containing compound;

all weights above being based on the total weight of the powder composition;

wherein the aqueous composition contains a cosmetically acceptable solvent selected from selected from water and a water/organic solvent mixture;

wherein the powder composition and/or the aqueous composition additionally contains from about 0.5% to about 5% by weight of at least one chelant compound; wherein the pH of the ready to use composition ranges from about 9 to about 14; and wherein the viscosity of the ready to use composition is from about 30 uD to about 100 uD; and 2) contacting the hair with the ready to use composition for a sufficient period of time to achieve a desired depilatory effect.

In yet another embodiment, the present invention relates to a multi-compartment kit for depilating hair comprising at least two compartments, wherein a first compartment comprises any one of the above-described powder compositions and wherein a second compartment comprises an aqueous composition containing a cosmetically acceptable solvent selected from selected from water and a water/organic solvent mixture.

It was surprisingly and unexpectedly discovered that when the powder composition of the invention was placed in contact with an aqueous composition, a thick, smooth, creamy and homogenous composition was obtained which could be employed as a ready to use composition for depilating hair.

It was also surprisingly and unexpectedly discovered that powder composition of the invention was stable over time and retained the hair removal or hair degradation activity of the sulfur-containing compound such that when it was contacted or mixed with an aqueous composition, the resulting ready to use composition effectively depilated hair after it was allowed to stand on the hair for a period of time.

Furthermore, it was surprisingly and unexpectedly discovered that even when a liquid fatty substance such as an oil was present even at high levels in the powder composition of the present invention, the powder or pulverent particles comprising the powder remained unaggregated and discrete such that the particles did not clump or stick. In addition, it was found that the powder flowed or poured easily and mixed easily with an aqueous composition.

It was also found that the ready to use compositions of the present invention have a thick, smooth and creamy texture, i.e., not lumpy and/or thin, are easy to apply and spread on the hair, and did not easily drip or run off of the hair fibers. The non-drip consistency of the ready to use compositions of the present invention is desirable because it helps prevent the compositions from coming in contact with and causing irritation on the skin or scalp.

These attributes of the ready to use compositions can also be characterized in terms of their viscosities which were found to range from about 30 uD to about 100 uD.

Alkaline Material

The present invention employs at least one alkaline material comprising at least one hydroxide-containing compound.

The at least one hydroxide-containing compound may be selected from alkali metal hydroxides, alkaline-earth metal hydroxides, transition metal hydroxides, and mixtures thereof.

In some embodiments, the at least one hydroxide-containing compound is selected from sodium hydroxide, potassium hydroxide, lithium hydroxide, calcium hydroxide, magnesium hydroxide, barium hydroxide, strontium hydroxide, manganese hydroxide, zinc hydroxide, and mixtures thereof.

In other embodiments, the at least one hydroxide-containing compound is selected from sodium hydroxide, potassium hydroxide, lithium hydroxide, calcium hydroxide, and mixtures thereof.

According to preferred embodiments, the at least one hydroxide-containing compound is calcium hydroxide.

The amount of the at least one hydroxide-containing compound is preferably such that when the powder composition is mixed with an aqueous composition, the resulting ready to use composition has a pH of greater than 7 and ranging from about 9 to about 14.

The at least one alkaline material comprising at least one hydroxide-containing compound can be employed in the powder compositions of the present invention in an amount ranging from about 1 to about 30% by weight of active material, based on the total weight of the composition, including all ranges and subranges therebetween.

In certain embodiments, the at least one alkaline material comprising at least one hydroxide-containing compound is employed in the powder compositions of the present invention in an amount ranging from about 1 to about 20% by weight, preferably from about 3 to about 20% by weight, more preferably from about 3 to about 10% by weight, or even more preferably from about 4 to about 8% by weight, with all weights of the alkaline material being the weight of the active material and based on the total weight of the composition, including all ranges and subranges therebetween.

In preferred embodiments, the at least one alkaline material comprising at least one hydroxide-containing compound is employed in an amount of about 15%, or about 12.5%, or about 12%, or about 10%, or about 8%, or about 6%, or about 5%, or about 4%, or about 2.5%, or about 2%, by weight, with all weights of the alkaline material being the weight of the active material and based on the total weight of the composition, including all ranges and subranges therebetween.

Carbonate Compound

The at least two carbonate compounds of the present invention are selected from calcium carbonate, lithium carbonate, sodium carbonate, potassium carbonate, guanidine carbonate, and mixtures thereof.

In some embodiments, the powder compositions employ two or more carbonate compounds selected from calcium carbonate, lithium carbonate, sodium carbonate, potassium carbonate, and guanidine carbonate.

In certain embodiments, the at least two carbonate compounds for use in the powder compositions of the present invention are calcium carbonate and guanidine carbonate.

In other embodiments, the powder compositions employ calcium carbonate and guanidine carbonate.

The at least two carbonate compounds are employed in the powder compositions of the present invention in a total amount ranging from about 20 to about 40% by weight, preferably from about 25 to about 35% by weight, more preferably from about 25 to about 30% by weight, based on the total weight of the composition, including all ranges and subranges therebetween.

In preferred embodiments, the at least two carbonate compounds are employed in a total amount of about 25%, or about 27.5%, or about 30%, or about 35% by weight, based on the total weight of the powder composition.

In certain embodiments, the at least two carbonate compounds for use in the powder compositions of the present invention are calcium carbonate and guanidine carbonate wherein calcium carbonate is present in an amount ranging from about 20 to about 40% by weight, preferably from about 25 to about 35% by weight, more preferably from about 25 to about 30% by weight, based on the total weight of the composition, including all ranges and subranges therebetween and guanidine carbonate is present in amount ranging from about 0.5 to about 2% by weight, preferably from about 1 to about 2% by weight, based on the total weight of the composition, including all ranges and subranges therebetween.

Starch

According to the present invention, the starch that may be used in the present invention consists more particularly of macromolecules in the form of polymers formed from elemental units that are anhydroglucose units. The number of these units and their assembly make it possible to distinguish amylose (linear polymer) and amylopectin (branched polymer). The relative proportions of amylose and of amylopectin, and their degree of polymerization, vary as a function of the plant origin of the starches.

The starch used in the present invention may originate from a plant source such as cereals, tubers, roots, legumes and fruit. Thus, the starch(es) may originate from a plant source chosen from corn, pea, potato, sweet potato, banana, barley, wheat, rice, oat, sago, tapioca and sorghum.

Starches are generally in the form of a white powder, which is insoluble in cold water, whose elemental particle size ranges from 3 to 100 microns. The starches used in the composition of the invention may be chemically modified via one or more of the following reactions: pregelatinization, oxidation, crosslinking, esterification, heat treatments.

More particularly, these reactions may be performed in the following manner:
 pregelatinization by splitting the starch granules (for example drying and cooking in a drying drum);
 oxidation with strong oxidizing agents, leading to the introduction of carboxyl groups into the starch molecule and to depolymerization of the starch molecule (for example by treating an aqueous starch solution with sodium hypochlorite);
 crosslinking with functional agents capable of reacting with the hydroxyl groups of the starch molecules, which will thus bond together (for example with glyceryl and/or phosphate groups);
 esterification in alkaline medium for the grafting of functional groups, especially C—I—C6 acyl (acetyl), d-C6 hydroxyalkyl (hydroxyethyl or hydroxypropyl), carboxy alkyl (in particular carboxymethyl) or octenylsuccinic. Mention is made in particular of starches modified with sodium carboxymethyl.

Monostarch phosphates (of the type Am-0-PO-(OX)2), distarch phosphates (of the type Am-O-PO-(OX)-O-Am) or even tristarch phosphates (of the type Am-O-PO-(0-Am)2) or mixtures thereof (Am meaning starch) may especially be obtained by crosslinking with phosphorus compounds.

X especially denotes alkali metals (for example sodium or potassium), alkaline-earth metals (for example calcium or magnesium), ammonium salts, amine salts, for instance those of monoethanolamine, diethanolamine, triethanolamine, 3-amino-1,2-propanediol, or ammonium salts derived from basic amino acids such as lysine, arginine, sarcosine, ornithine or citrulline.

The phosphorus compounds may be, for example, sodium tripolyphosphate, sodium orthophosphate, phosphorus oxychloride or sodium trimetaphosphate. Starch phosphates, in particular hydroxypropyl starch phosphates, or compounds rich in starch phosphate and in particular in hydroxypropyl starch phosphate can be used.

When the starches are chemically modified via an esterification reaction, carboxyalkyl starches are obtained.

The carboxyalkyl starches are preferably carboxy($C_1$-$C_4$) alkyl starch and more particularly carboxymethyl starches.

The salts are especially salts of alkali metals or alkaline-earth metals such as Na, K ½, Li, NH4, or salts of a quaternary ammonium or of an organic amine such as monoethanolamine, diethanolamine or triethanolamine.

Carboxyalkyl starches are obtained by grafting carboxyalkyl groups onto one or more alcohol functions of starch, especially by reaction of starch and of sodium monochloroacetate in alkaline medium.

The carboxyalkyl groups are generally attached via an ether function, more particularly to carbon 1.

The degree of substitution preferably ranges from 0.1 to 1 and more particularly from 0.15 to 0.5. The degree of substitution is defined according to the present invention as being the mean number of hydroxyl groups substituted with an ester or ether group (in the present case ether for the carboxymethyl starches) per monosaccharide unit of the polysaccharide.

According to the invention, it is also possible to use amphoteric starches, these amphoteric starches containing one or more anionic groups and one or more cationic groups. The anionic and cationic groups may be linked to the same reactive site of the starch molecule or to different reactive sites; they are preferably linked to the same reactive site. The anionic groups may be of carboxylic, phosphate or sulfate type, preferably carboxylic. The cationic groups may be of primary, secondary, tertiary or quaternary amine type.

According to the invention, the at least one starch may also be selected from hydrolyzed starches, for example, dextrins and maltodextrins.

Maltrodextrins and dextrins may be characterized with a Dextrose equivalent (DE) which is the relative sweetness of sugars, oligosaccharides, or blends compared to dextrose, both expressed as a percentage. For example, a maltodextrin with a DE of 10 would be 10 percent as sweet as dextrose (DE=100), while sucrose, with a DE of 120, would be 1.2 times as sweet as dextrose. For solutions made from starch, it is an estimate of the percentage reducing sugars present in the total starch product. The DE describes the degree of conversion of starch to dextrose: starch is close to 0, glucose/dextrose is 100 (percent), dextrins vary between 1 and 13, and maltodextrins vary between 3 and 20. The DE gives an indication of the average degree of polymerisation (DP) for starch sugars. The rule of thumb is DExDP=120.

According to the present invention, a preferred starch for use in the powder composition may be chosen from corn starch, potato starch, dextrin, maltodextrin, and mixtures thereof.

In preferred embodiments, the starch is chosen from corn starch, maltodextrin, and mixtures thereof. Corn starch is available from the company Roquette under the tradename Amidon de Mais B. Maltodextrin is available from the company Grain Processing Corporation under the tradename Maltrin M100.

In some preferred embodiments, the starch for use in the powder composition of the present invention is corn starch.

In other preferred embodiments, the starch for use in the powder composition of the present invention is maltodextrin.

The at least one starch present is employed in the powder compositions of the present invention in an amount ranging from about 1 to about 25% by weight, or such as from about 1 to about 12% by weight, or such as from about 3 to about 10% by weight, based on the total weight of the composition, including all ranges and subranges therebetween.

In preferred embodiments, the at least one starch may be present in an amount of about 10% or about 5% or about 3%, based on the total weight of the powder composition.

Silica Material

According to the present invention, the silica material comprises silica particles that can be hydrophilic or hydrophobic silicas or mixtures thereof.

Hydrophilic silicas in accordance with the present invention are not only pure hydrophilic silica particles but also particles which are wholly or partly coated with hydrophilic silica.

The hydrophilic silicas which can be used in the composition of the invention are preferably amorphous. They may be of pyrogenic or precipitated origin. They can also be in powder form or in aqueous dispersion.

The fumed hydrophilic silicas are obtained by continuous flame pyrolysis at 1000 degrees centigrade of silicon tetrachloride ($SiCl_4$) in the presence of hydrogen and of oxygen.

The precipitated silicas are obtained by reacting an acid with solutions of alkali silicates, preferably sodium silicate. According to one preferred embodiment of the invention, the hydrophilic silica(s) are chosen from silicas having a specific surface area of from 30 to 500 $m^2/g$, a number-average particle size ranging from 3 to 50 nm and a packed density ranging from 40 to 200 and better still from 50 to 150 g/l. These silicas are sold by the company Degussa-Hips under the names Aerosil 90, Aerosil 130, Aerosil 150, Aerosil 200, Aerosil 300, Aerosil 380, Aerosil OX50 and Aerosil 320DS.

It is also possible to use silica as an aqueous dispersion, and for example a dispersion of colloidal silica, such as the product sold under the name Bindzil 30/220® by the company Eka Chemicals, which is a colloidal dispersion of amorphous silica (size: 14 nanometers) in water (30/70) or such as the product sold under the INCI name hydrated silica and tradename Elfadent® SM 514 by the company Grace Davison.

The hydrophilic silica which can be used according to the invention can also consist of a particle comprising a silica surface, for example a particle totally or partially covered with silica, in particular a mineral particle totally or partially covered with silica. Use is preferably made, as hydrophilic silica, of fumed silicas and in particular those sold under the names Aerosil 200® and Aerosil 300® by the company Degussa-Hijls.

The hydrophobic silicas can be amorphous hydrophobic silicas of fumed origin. The amorphous hydrophobic silicas of fumed origin are obtained from hydrophilic silicas. As described above, the latter are obtained by continuous flame pyrolysis at 1000° C. of silicon tetrachloride ($SiCl_4$) in the presence of hydrogen and of oxygen. They are then made hydrophobic by means of a treatment with halogenated silanes, alkoxysilanes or silazanes. The hydrophobic silicas differ from the starting hydrophilic silicas, inter alia, by virtue of a lower silanol group density and by virtue of a lower water vapour adsorption.

The hydrophobic silica(s) may be chosen from silicas having a specific surface area of from 50 to 500 $m^2/g$, a number-average particle size ranging from 3 to 50 nm and a packed density ranging from 40 to 200 and better still from 50 to 150 g/l. These silicas are sold by the company Degussa-Hips under the names Aerosil R202, Aerosil R805, Aerosil R812, Aerosil R972 and Aerosil R974.

The hydrophobic silica which can be used according to the invention can also consist of a particle totally or partially covered with hydrophobic silica, in particular a mineral particle totally or partially covered with hydrophobic silica, such as pigments and metal oxides covered with hydrophobic silica. Use is preferably made, as hydrophobic silica, of the product sold under the name Aerosil R972® by the company Degussa-Hijls.

Other examples of silica particles comprise silica powders that include:

porous silica microspheres, especially those sold under the names Sunsphere® H53 and Sunsphere® H33 by the company Asahi Glass; MSS-500-3H by the company Kobo;

polydimethylsiloxane-coated amorphous silica microspheres, especially those sold under the name SA Sunsphere® H33 by the company Asahi Glass;

amorphous hollow silica particles, especially those sold under the name Silica Shells by the company Kobo; and precipitated silica powders surface-treated with a mineral wax, such as precipitated silica treated with a polyethylene wax, and especially those sold under the name Acematt® OK 412 by the company Evonik-Degussa.

Other suitable silica particles of the invention are hydrophobic silica aerogel particles (also called "aerogels").

Aerogels are ultra-light porous materials. They are generally synthesized via a sol-gel process in a liquid medium and then dried, usually by extraction with a supercritical fluid, the one most commonly used being supercritical $CO_2$. This type of drying makes it possible to avoid shrinkage of the pores and of the material. Other types of drying also make it possible to obtain porous materials starting from gel, namely cryodesiccation, which consists in solidifying the gel at low temperature and in then subliming the solvent, and drying by evaporation. The materials thus obtained are referred to respectively as cryogels and xerogels.

The aerogel particles in accordance with the present invention are hydrophobic aerogel particles.

The term "hydrophobic aerogel particle" means any particle of the aerogel type having a water absorption capacity at the wet point of less than 0.1 ml/g, i.e. less than 10 g of water per 100 g of particle.

The wet point corresponds to the amount of water that needs to be added to 1 g of particle in order to obtain a homogeneous paste. This method is derived directly from the method for determining the oil uptake of a powder as described in standard NF T 30-022. The measurements are taken in the same manner by means of the wet point and the flow point, which have, respectively, the following definitions:

wet point: weight expressed in grams per 100 g of product corresponding to the production of a homogeneous paste during the addition of a solvent to a powder.

The wet point is measured according to the following protocol:

Equipment Used:
Glass plate (25×25 mm)
Spatula (wooden shaft and metal part, 15×2.7 mm)
Silk-bristled brush
Balance The glass plate is placed on the balance and 1 g of aerogel is weighed out. The beaker containing the solvent and the liquid sampling pipette is placed on the balance. The solvent is gradually added to the powder, the whole being regularly blended (every 3 to 4 drops) with the spatula. The mass of solvent required to reach the wet point is noted. The average of three tests will be determined.

The hydrophobic aerogels used according to the present invention may be organic, inorganic or organic-inorganic hybrid aerogels.

The organic aerogels may be based on resins from among the following: polyurethanes, resorcinol-formaldehyde, polyfurfuranol, cresol-formaldehyde, phenol-furfuranol, polybutadiene, melamine-formaldehyde, phenol-furfural, polyimides, polyacrylates, polymethacrylates, polyolefins, polystyrenes, polyacrylonitriles, phenol-formaldehyde, polyvinyl alcohol, dialdehydes, polycyanides, epoxys, celluloses, cellulose derivatives, chitosan, agar, agarose, alginate, starches, and mixtures thereof.

Aerogels based on organic-inorganic hybrids, for example silica-PMMA, silica-chitosan and silica-polyether, are also envisaged. Patent applications US 2005/0192366 and WO 2007/126410 describe such organic-inorganic hybrid materials.

The hydrophobic aerogel particles used in the present invention have a specific surface area per unit of mass (SM) ranging from 200 to 1500 m2/g, preferably from 600 to 1200 m2/g and better still from 600 to 800 m2/g, and a size, expressed as the volume-mean diameter (D[0.5]), of less than 1500 μm and preferably ranging from 1 to 30 μm, more preferably from 5 to 25 μm, better still from 5 to 20 μm and even better still from 5 to 15 μm.

The specific surface area per unit of mass can be determined by the nitrogen absorption method, known as the BET (Brunauer-Emmett-Teller) method, described in The Journal of the American Chemical Society, Vol. 60, page 309, February 1938. The BET specific surface area corresponds to the total specific surface area of the particles under consideration.

The sizes of the aerogel particles according to the invention can be measured by static light scattering using a commercial particle size analyser such as the MasterSizer 2000 machine from Malvern. The data are processed on the basis of the Mie scattering theory.

According to an advantageous embodiment, the hydrophobic aerogel particles used in the present invention have a specific surface area per unit of mass (SM) ranging from 600 to 800 m2/g and a size, expressed as the volume-mean diameter (D[0.5]), ranging from 5 to 20 μm and better still from 5 to 15 μm.

The hydrophobic aerogel particles used in the present invention may advantageously have a tapped density ☐ ranging from 0.02 g/cm3 to 0.10 g/cm3 and preferably from 0.02 g/cm3 to 0.08 g/cm3.

In the context of the present invention, this density may be assessed according to the following protocol, known as the tapped density protocol:

40 g of powder are poured into a measuring cylinder; the measuring cylinder is then placed on the Stay 2003 machine from Stampf Volumeter; the measuring cylinder is subsequently subjected to a series of 2500 tapping actions (this operation is repeated until the difference in volume between 2 consecutive tests is less than 2%); and then the final volume Vf of tapped powder is measured directly on the measuring cylinder. The tapped density is determined by the ratio m/Vf, in this instance 40/Vf (Vf being expressed in cm3 and min g).

According to one embodiment, the hydrophobic aerogel particles used in the present invention have a specific surface area per unit of volume SV ranging from 5 to 60 m2/cm3, preferably from 10 to 50 m2/cm3 and better still from 15 to 40 m2/cm3.

The specific surface area per unit of volume is given by the relationship: $SV=SM \cdot \rho$ where $\rho$ is the tapped density expressed in g/cm3 and SM is the specific surface area per unit of mass expressed in m2/g, as defined above.

Preferably, the hydrophobic aerogel particles according to the invention have an oil-absorbing capacity, measured at the wet point, ranging from 5 to 18 ml/g, preferably from 6 to 15 ml/g and better still from 8 to 12 ml/g.

The absorption capacity measured at the wet point, denoted Wp, corresponds to the amount of oil that needs to be added to 100 g of particles in order to obtain a homogeneous paste.

It is measured according to the "wet point" method or method for determining the oil uptake of a powder as described in standard NF T 30-022. It corresponds to the amount of oil adsorbed onto the available surface of the powder and/or absorbed by the powder by measurement of the wet point, described below:

An amount m=2 g of powder is placed on a glass plate and the oil (isononyl isononanoate) is then added dropwise. After addition of 4 to 5 drops of oil to the powder, mixing is performed using a spatula, and addition of oil is continued until conglomerates of oil and powder have formed. From this point, the oil is added one drop at a time and the mixture is then triturated with the spatula. The addition of oil is stopped when a firm and smooth paste is obtained. This paste must be able to be spread over the glass plate without cracks or the formation of lumps. The volume Vs (expressed in ml) of oil used is then noted.

The oil uptake corresponds to the ratio Vs/m.

According to a particular embodiment, the aerogel particles used are inorganic and are more particularly hydrophobic silica aerogel particles having the properties stated previously.

Silica aerogels are porous materials obtained by replacing (especially by drying) the liquid component of a silica gel with air.

They are generally synthesized via a sol-gel process in a liquid medium and then dried, usually by extraction with a supercritical fluid, the one most commonly used being supercritical CO2. This type of drying makes it possible to avoid shrinkage of the pores and of the material.

The hydrophobic silica aerogels used according to the present invention are preferably silylated silica aerogels (INCI name: silica silylate).

The term "hydrophobic silica" means any silica whose surface is treated with silylating agents, for example halogenated silanes such as alkylchlorosilanes, siloxanes, in particular dimethylsiloxanes such as hexamethyldisiloxane, or silazanes, so as to functionalize the OH groups with silyl groups Si—Rn, for example trimethylsilyl groups.

As regards the preparation of hydrophobic silica aerogel particles that have been surface-modified by silylation, reference may be made to document U.S. Pat. No. 7,470,725.

Use will in particular be made of the hydrophobic silica aerogel particles that have been surface-modified with trimethylsilyl groups.

As hydrophobic silica aerogels that may be used in the invention, examples that may be mentioned include the aerogel sold under the name VM-2260 (INCI name: Silica silylate) by Dow Corning, the particles of which have a mean size of about 1000 microns and a specific surface area per unit of mass ranging from 600 to 800 m2/g.

Mention may also be made of the aerogels sold by Cabot under the references Aerogel TLD 201, Aerogel OGD 201 and Aerogel TLD 203, Enova® Aerogel MT 1100 and Enova Aerogel MT 1200.

The silica particles may also be natural and non-treated. Suitable examples are those known under the trade names SILLITIN N85, SILLITIN N87, SILLITIN N82, SILLITIN V85 and SILLITIN V88, commercially available from the company Hoffmann Mineral.

According to the present invention, a preferred silica particle is hydrated silica, such as that sold under the tradename Elfadent® SM 514 by the company Grace Davison.

According to the present invention, other preferred silica particles are hydrophobic silica aerogel particles or aerogel sold under the name VM-2270 (INCI name: Silica silylate, 98% active), by the company Dow Corning, the particles of which have a mean size ranging from 5-15 microns and a specific surface area per unit of mass ranging from 600 to 800 m2/g (oil uptake equal to 1080 ml/100 g).

In some embodiments, the silica material in the powder compositions of the present invention may employ one or more of the different types of the above-described silica particles.

The silica material comprising silica particles may be present in the powder compositions of the present invention in a total amount ranging from about 0.1 to about 20% by weight, such as from about 0.1 to about 16% by weight, or such as from about 0.1 to about 10% by weight, or such as from about 0.1 to about 5% by weight, based on the total weight of the powder composition, including all ranges and subranges therebetween.

In preferred embodiments, the silica material may be present in the powder compositions of the present invention in a total amount ranging from about 0.1 to about 5% by weight, or such as from about 0.5 to about 4% by weight, or such as from about 0.5 to about 3% by weight, or such as from about 0.5 to about 2% by weight, based on the total weight of the powder composition, including all ranges and subranges therebetween.

In yet other preferred embodiments, the at least one silica material is chosen from hydrophobic silica aerogels and is employed in an amount ranging from about 0.5 to about 3% by weight, or of about 3% or of about 2.5% or of about 2% or about 1.5% or about 1% or about 0.5% by weight, based on the total weight of the powder composition.

Liquid Fatty Substances

The compositions of the present invention comprise at least one liquid fatty substance, i.e. a compound that is liquid at a temperature of 25 degrees centigrade and at atmospheric pressure (also called "oil").

The term "fatty substance" means an organic compound that is insoluble in water at ordinary temperature (25 degrees C.) and at atmospheric pressure (760 mmHg) (solubility of less than 5 percent, preferably less than 1 percent and even more preferentially less than 0.1 percent). They exhibit, in their structure, at least one hydrocarbon chain comprising at least 6 carbon atoms or a sequence of at least two siloxane groups. In addition, the fatty substances are generally soluble in organic solvents under the same temperature and pressure conditions, for instance chloroform, dichloromethane, carbon tetrachloride, ethanol, benzene, toluene, tetrahydrofuran (THF), liquid petroleum jelly or decamethylcyclopentasiloxane. The fatty substances of the invention do not contain any salified or unsalified carboxylic acid groups (COOH or COO—).

The term "non-silicone o/V means an oil not containing any silicon atoms (Si) and the term "silicone o/V means an oil containing at least one silicon atom.

More particularly, the liquid fatty substances are chosen from $C_6$-$C_{16}$ hydrocarbons, hydrocarbons containing more than 16 carbon atoms, particularly linear or branched hydrocarbons of mineral or synthetic origin having more than 16 carbon atoms, non-silicone oils of animal origin, plant oils of triglyceride type, synthetic triglycerides, fluoro oils, liquid fatty alcohols, liquid fatty acid and/or liquid fatty alcohol esters other than triglycerides and plant waxes, silicones oils, and mixtures thereof.

The fatty alcohols, esters and acids more particularly have at least one linear or branched, saturated or unsaturated hydrocarbon-based group comprising 6 to 30 and better still from 8 to 30 carbon atoms, which is optionally substituted, in particular with one or more hydroxyl groups (in particular 1 to 4). If they are unsaturated, these compounds may comprise one to three conjugated or unconjugated carbon-carbon double bonds.

As regards the $C_6$-$C_{16}$ hydrocarbons, they are linear, branched or optionally cyclic, and are preferably alkanes. Examples that may be mentioned include hexane, dodecane and isoparaffins such as isohexadecane and isodecane.

A hydrocarbon-based oil of animal origin that may be mentioned is perhydrosqualene.

The triglyceride oils of plant or synthetic origin are preferably chosen from liquid fatty acid triglycerides containing from 6 to 30 carbon atoms, for instance heptanoic or octanoic acid triglycerides, or alternatively, for example, sunflower oil, corn oil, soybean oil, marrow oil, grapeseed oil, sesame seed oil, hazelnut oil, apricot oil, macadamia oil, arara oil, castor oil, avocado oil, caprylic/capric acid triglycerides, for instance those sold by the company Stearineries Dubois or those sold under the names Miglyol® 810, 812 and 818 by the company Dynamit Nobel, jojoba oil and shea butter oil.

The linear or branched hydrocarbons of mineral or synthetic origin having more than 16 carbon atoms are preferably chosen from liquid paraffins, petroleum jelly, liquid petroleum jelly, polydecenes or hydrogenated polyisobutene, such as Parleam®. The fluoro oils that may be chosen from perfluoromethylcyclopentane and perfluoro-1,3-dimethylcyclohexane, sold under the names Flutec® PC1 and Flutec® PC3 by the company BNFL Fluorochemicals; perfluoro-1,2-dimethylcyclobutane; perfluoroalkanes such as dodecafluoropentane and tetradecafluorohexane, sold under the names PF 5050® and PF 5060® by the company 3M, or bromoperfluorooctyl sold under the name Foralkyl® by the company Atochem; nonafluoromethoxybutane and nonafluoroethoxyisobutane; perfluoromorpholine derivatives such as 4-trifluoromethyl perfluoromorpholine sold under the name PF 5052® by the company 3M.

The liquid fatty alcohols which are suitable for the implementation of the invention are more particularly chosen from saturated or unsaturated, linear or branched alcohols comprising from 6 to 30 carbon atoms and preferably from 8 to 30 carbon atoms. Mention may be made, for example, of octyldodecanol, 2-butyloctanol, 2-hexyldecanol, 2-undecylpentadecanol, oleyl alcohol or linoleyl alcohol.

As regards the liquid fatty acids, mention may be made especially of saturated or unsaturated carboxylic acids comprising from 6 to 30 carbon atoms, and preferably from 9 to 30 carbon atoms, preferably chosen from oleic acid, linoleic acid, linolenic acid and isostearic acid. Theses acids are not under the form of salts, i.e. if present, the composition may not contain organic or mineral alkaline agents such as sodium hydroxide, potassium hydroxide, monoethanolamine, triethanolamine.

As regards the liquid esters of a fatty acid and/or fatty alcohols, which are advantageously different from the triglycerides mentioned previously, mention may be made especially of liquid esters of saturated or unsaturated, linear or branched $C_1$-$C_{26}$ aliphatic monoacids or polyacids and of saturated or unsaturated, linear or branched $C_1$-$C_{26}$ aliphatic monoalcohols or polyalcohols, the total carbon number of the esters being greater than or equal to 6 and more advantageously greater than or equal to 10.

Among the monoesters, mention may be made of; isocetyl stearate; isodecyl neopentanoate; isostearyl neopentanoate; 2-ethylhexyl isononanoate; ethyl and isopropyl palmitates, alkyl myristates such as isopropyl, ethyl, myristate.

Still within the context of this variant, esters of $C_4$-$C_{22}$ dicarboxylic or tricarboxylic acids and of $C_1$-$C_{22}$ alcohols and esters of mono-, di- or tricarboxylic acids and of $C_2$-$C_{26}$ di-, tri-, tetra- or pentahydroxy alcohols may also be used.

Mention may be made especially of: diethyl sebacate; diisopropyl sebacate; diisopropyl adipate; di-n-propyl adipate; dioctyl adipate; diisostearyl adipate; dioctyl maleate; glyceryl undecylenate; octyldodecyl stearoyl stearate; pentaerythrityl monoricinoleate; pentaerythrityl tetraisononanoate; pentaerythrityl tetrapelargonate; pentaerythrityl tetraisostearate; pentaerythrityl tetraoctanoate; propylene glycol dicaprylate; propylene glycol dicaprate; tridecyl erucate; triisopropyl citrate; triisostearyl citrate; glyceryl trilactate; glyceryl trioctanoate; trioctyldodecyl citrate; trioleyl citrate; propylene glycol dioctanoate; neopentyl glycol diheptanoate; diethylene glycol diisononanoate; and polyethylene glycol distearates.

Among the esters mentioned above, it is preferred to use ethyl, isopropyl, myristyl, cetyl or stearyl palmitate, 2-ethylhexyl palmitate, 2-octyldecyl palmitate, alkyl myristates such as isopropyl, butyl, cetyl or 2-octyldodecyl myristate, hexyl stearate, butyl stearate, isobutyl stearate; dioctyl malate, hexyl laurate, 2-hexyldecyl laurate, isononyl isononanoate or cetyl octanoate.

The composition may also comprise, as liquid fatty ester, sugar esters and diesters of $C_6$-$C_{30}$ and preferably $C_{12}$-$C_{22}$ fatty acids. It is recalled that the term "sugar" means oxygen-bearing hydrocarbon-based compounds which have several alcohol functions, with or without aldehyde or ketone functions, and which comprise at least 4 carbon atoms. These sugars can be monosaccharides, oligosaccharides or polysaccharides.

Mention may be made, as suitable sugars, for example, of sucrose (or saccharose), glucose, galactose, ribose, fucose, maltose, fructose, mannose, arabinose, xylose and lactose, and derivatives thereof, in particular alkyl derivatives, such as methyl derivatives, for instance methylglucose.

The sugar esters of fatty acids may be chosen in particular from the group comprising the esters or mixtures of esters of sugars described previously and of linear or branched, saturated or unsaturated $C_6$-$C_{30}$ and preferably $C_{12}$-$C_{22}$ fatty acids. If they are unsaturated, these compounds may comprise one to three conjugated or unconjugated carbon-carbon double bonds.

The esters according to this variant may also be chosen from mono-, di-, tri- and tetraesters, polyesters, and mixtures thereof.

These esters can, for example, be oleates, laurates, palmitates, myristates, behenates, cocoates, stearates, linoleates, linolenates, caprates, arachidonates or mixtures thereof, such as, in particular, oleate/palmitate, oleate/stearate or palmitate/stearate mixed esters.

More particularly, use is made of monoesters and diesters and in particular mono- or di-oleate, -stearate, -behenate, -oleate/palmitate, -linoleate, -linolenate or -oleate/stearate of sucrose, of glucose or or of methylglucose.

An example that may be mentioned is the product sold under the name Glucate® DO by the company Amerchol, which is a methylglucose di-oleate.

The silicones oils that may be used in the powder composition of the present invention are volatile or non-volatile, cyclic, linear or branched silicones, which are unmodified or modified with organic groups, having a viscosity from $5\times10^{-6}$ to 2.5 m$^2$/s at 25 degrees centigrade, and preferably $1\times10^{-5}$ to 1 m$^2$/s.

Preferably, the silicone is chosen from liquid polydialkylsiloxanes, especially polydimethylsiloxanes (PDMS), and liquid organomodified polysiloxanes comprising at least one functional group chosen from amino groups and alkoxy groups.

Organopolysiloxanes are defined in greater detail in Walter Noll's Chemistry and Technology of Silicones (1968), Academic Press. They may be volatile or non-volatile.

When they are volatile, the silicones are more particularly chosen from those having a boiling point of between 60 degrees centigrade and 260 degrees centigrade, and more particularly still from:

(i) cyclic polydialkylsiloxanes containing from 3 to 7 and preferably from 4 to 5 silicon atoms. These are, for example, octamethylcyclotetrasiloxane sold in particular under the name Volatile Silicone® 7207 by Union Carbide or Silbione® 70045 V2 by Rhodia, decamethylcyclopentasiloxane sold under the name Volatile Silicone® 7158 by Union Carbide, and Silbione® 70045 V5 by Rhodia, and mixtures thereof.

Mention may also be made of cyclocopolymers of the dimethylsiloxane/methylalkylsiloxane type, such as Volatile Silicone® FZ 3109 sold by the company Union Carbide.

Mention may also be made of mixtures of cyclic polydialkylsiloxanes with organosilicon compounds, such as the mixture of octamethylcyclotetrasiloxane and tetra(trimethylsilyl)pentaerythritol (50/50) and the mixture of octamethylcyclotetrasiloxane and oxy-1,1'-bis(2,2,2',2',3,3'-hexatrimethylsilyloxy)neopentane;

(ii) linear volatile polydialkylsiloxanes containing 2 to 9 silicon atoms and having a viscosity of less than or equal to $5\times10^{-6}$ m2/s at 25 degrees centigrade An example is decamethyltetrasiloxane sold in particular under the name SH 200 by the company Toray Silicone.

Use may be made of non-volatile polydialkylsiloxanes, among which mention may be made mainly of polydimethylsiloxanes having trimethylsilyl end groups. The viscosity of the silicones is measured at 25 degrees centigrade according to ASTM standard 445 Appendix C.

Mention may be made, among these polydialkylsiloxanes, without implied limitation, of the following commercial products:

the Silbione® oils of the 47 and 70 047 series or the Mirasil® oils sold by Rhodia, such as, for example, the oil 70 047 V 500 000;

the oils of the Mirasil® series sold by Rhodia;

the oils of the 200 series from the company Dow Corning, such as DC200 with a viscosity of 60 000 mm2/s;

the Viscasil® oils from General Electric and certain oils of the SF series (SF 96, SF 18) from General Electric.

Mention may also be made of polydimethylsiloxanes bearing dimethylsilanol end groups known under the name dimethiconol (CTFA), such as the oils of series 48 from the company Rhodia.

The liquid fatty substances are advantageously chosen from $C_6$-$C_{16}$ alkanes, non-silicone oils of plant, mineral or synthetic origin, liquid fatty alcohols, liquid fatty acids and liquid esters of a fatty acid and/or of a fatty alcohol, or mixtures thereof.

Preferably, the liquid fatty substance is chosen from liquid petroleum jelly, $C_6$-$C_{16}$ alkanes, polydecenes, liquid esters of a fatty acid and/or of a fatty alcohol, and liquid fatty alcohols, or mixtures thereof.

A preferred liquid fatty substance for use in the present invention is mineral oil which may be commercially available from the supplier Sonneborn under the tradename Kaydol® Heavy White Mineral Oil or from the supplier Exxonmobil Chemical under the tradename Primol™ 352 or from Sonneborn under the tradename Blandol, or from Armedsa under the tradename Aemoil M-302CG or from Exxonmobil Chemical under the tradename Marcol 82.

The at least one liquid fatty substance is present in the powder composition of the present invention in an amount ranging from about 5 to about 50% by weight and preferably in an amount ranging from about 5 to about 40% by weight, more preferably from about 6 to about 30% by weight, even more preferably from about 6 to about 26% by weight, based on the total weight of the powder composition, including all ranges and subranges therebetween.

In some embodiments, the at least one liquid fatty substance is employed in the powder composition of the present invention in an amount of at least about 5%, or at least about 10% by weight, or at least about 20% by weight, or at least about 25% by weight, or at least about 30% by weight, or at least about 35% by weight, based on the total weight of the powder composition In other embodiments, the at least one liquid fatty substance is employed in the powder composition of the present invention in an amount ranging from about 10 to about 30% by weight, or from about 20 to about 30% by weight, or from about 20 to about 26% by weight, based on the total weight of the powder composition, including all ranges and subranges therebetween.

In yet other embodiments, the at least one liquid fatty substance may be employed in an amount of about 26%, or about 20%, or about 10%, or about 6%, or about 5%, based on the total weight of the powder composition.

Acrylic Polymer

The at least one acrylic polymer of the present invention is preferably chosen from crosslinked acrylic polymers. Crosslinked acrylic polymers can be selected from modified or unmodified carboxyvinyl polymers, such as copolymers of acrylic acid and of C10-C30 alkyl acrylate or methacrylate, for instance the products sold under the tradenames Carbopol® and Pemulen™ (INCI names: carbomer, acrylates/C10-30 alkyl acrylate crosspolymer) by the company Lubrizol, or such as the crosslinked sodium polyacrylate sold under the name Cosmedia SP by the company Cognis (BASF) (INCI name: sodium polyacrylate).

Among the crosslinked acrylic polymers, sodium polyacrylate, carbomer, and acrylates/C10-30 alkyl acrylate crosspolymer are preferably used.

In some embodiments, the crosslinked acrylic polymer, sodium polyacrylate, is particularly preferred.

In other embodiments, the crosslinked acrylic polymers are preferably chosen from acrylates/C10-30 alkyl acrylate crosspolymer.

In certain embodiments, the crosslinked acrylic polymers are chosen from sodium polyacrylate, acrylates/C10-30 alkyl acrylate crosspolymer, and mixtures thereof.

The at least one acrylic polymer is employed in the powder composition of the present invention in an amount ranging from about 0.5 to about 15% by weight and preferably from about 1 to about 10% by weight, or preferably from about 1 to about 9% by weight, more preferably from about 2 to about 8.7% by weight, and even more preferably from about 2.4 to about 8.7% by weight, based on the total weight of the composition, including all ranges and subranges therebetween.

In some embodiments, the at least one acrylic polymer is employed in the powder composition of the present invention in an amount of about 8.7%, or about 4%, or about 3.5% by weight, based on the total weight of the powder composition.

Sulfur-Containing Compound

The sulfur-containing compound for use in the powder compositions of the invention may be selected from calcium thioglycolate, potassium thioglycolate, sodium thioglycolate, ammonium thioglycolate, strontium thioglycolate, magnesium thioglycolate, diammonium dithiodiglycolate, 2-methoxyethyl thioglycolate, 2-ethoxyethyl thioglycolate, 2-ethoxypropyl thioglycolate, methyl thioglycolate, ethyl thioglycolate, butyl thioglycolate, isooctyl thioglycolate, isopropyl thioglycolate, guanidine thioglycolate, glyceryl monothioglycolate, monoethanolamine thioglycolate, monoethanolamine thioglycolic acid, diammoniumdithiodiglycolate, dithioerythritol, thioglycerol, thioglycol, thioxanthine, thiosalicylic acid, N-acetyl-L-cysteine, lipoic acid, sodium dihydrolipoate 6,8-dithioocatanoate, sodium 6,8-diothioocatanoate, a hydrogen sulphide salt, thioglycolic acid, 2-mercaptopropionic acid, 3-mercaptopropionic acid, thiomalic acid, ammonium thiolactate, monoethanolamine thiolactate, thioglycolamide, homocysteine, cysteine, gluta-thione, dithiothreitol, dihydrolipoic acid, 1,3-dithiopropanol, thioglycolamide, glycerylmonothioglycolate, thioglycolhydrazine, cysteamine, and mixtures thereof.

In certain embodiments, the sulfur-containing compound is selected from calcium thioglycolate, potassium thioglycolate, ammonium thioglycolate, and mixtures thereof.

In certain other embodiments, the sulfur-containing compound is calcium thioglycolate.

The sulfur-containing compound is employed in the powder compositions of the present invention in an amount ranging from about 5 to about 20% by weight, preferably from about 8 to about 15% by weight, and more preferably from about 10 to about 15% by weight, based on the total weight of the composition, including all ranges and subranges therebetween.

In preferred embodiments, the at least one sulfur-containing compound is employed in an amount of about 8%, or about 10%, or about 15%, by weight, based on the total weight of the powder composition.

Wax

The powder composition of the present invention may further comprise at least one wax chosen from waxes that are solid or semisolid at room temperature. Preferably, the at least one wax of the present invention has a melting point at about or greater than 30° C., such as from between greater than 35° C. to about 250° C. or such as from between about 40° C. to about 100° C. The at least one wax is defined as having a reversible change of solid/liquid state. The melting point of a wax in solid form is the same as the freezing point of its liquid form, and depends on such factors as the purity of the substance and the surrounding pressure. The melting point is the temperature at which a solid and its liquid are in equilibrium at any fixed pressure. A solid wax begins to soften at a temperature close to the melting point of the wax. With increasing temperature, the wax continues to soften/melt until at a particular temperature, the wax completely becomes liquid at a standard atmospheric pressure. It is at this stage that an actual melting point value is given for the material under consideration. When heat is removed, the liquefied wax material begins to solidify until the material is back in solid form. By bringing the wax material to the liquid state (melting), it is possible to make it miscible with other materials such as oils, and to form a microscopically homogeneous mixture. However, when the temperature of the mixture is brought to room temperature, recrystallization of the wax with the other materials in the mixture may be obtained.

The melting points of the wax(e)s of the present invention may be determined according to known methods or apparatus such as by differential scanning calorimetry, Banc Koffler device, melting point apparatus, and slip melting point measurements.

The wax(es) of the present invention may be chosen from waxes that have hardness values ranging from about 0.001 MPa (Mega Pa) to about 15 MPa, or such as from about 1 MPa to about 12 MPa, or such as from about 3 MPa to about 10 MPa.

The hardness of the wax may be determined by any known method or apparatus such as by needle penetration or using the durometer or texturometer.

The wax of the present invention is chosen from natural waxes and synthetic waxes. Waxes may also be known as solid lipids.

Natural waxes include animal, vegetable/plant, mineral, or petroleum derived waxes. They are typically esters of fatty acids and long chain alcohols. Wax esters are derived from a variety of carboxylic acids and a variety of fatty alcohols.

Examples of waxes of the present invention include, but are not limited to, beeswax, hydrogenated alkyl olive esters (commercially available under the trade name phytowax olive; e.g., hydrogenated myristyl olive esters and hydrogenated stearyl olive esters), carnauba wax, candelilla wax, ouricoury wax, Japan wax, cork fibre wax or sugar cane wax, rice wax, rice bran wax, montan wax, paraffin wax, lignite wax or microcrystalline wax, ceresin or ozokerite, palm kernel glycerides/hydrogenated palm glycerides, palm butter, sumac wax, citrus aurantium *dulcis* (orange) peel wax, *theobroma grandiflorum* seed butter, *helianthus annuus* (Sunflower) seed wax, siliconyl candellila wax, and hydrogenated oils such as hydrogenated castor oil or jojoba oil, sugarcane, retamo, bayberry, soy, castor, esparto, hydroxyoctacosanyl hydroxystearate, Chinese wax, cetyl palmitate, lanolin, shellac, spermaceti, hydrogenated castor wax; synthetic waxes such as those of the hydrocarbon type and polyethylene waxes obtained from the polymerization or copolymerization of ethylene, polypropylene waxes, and Fischer-Tropsch® waxes, or else esters of fatty acids, such as octacosanyl stearate, glycerides which are solid at temperatures of above 35° C., poly(di)methylsiloxane esters which are solid at 30° C. and whose ester chain comprising at least 10 carbon atoms, or else di(1,1,1-trimethylolpropane) tetrastearate, which is sold or manufactured by Heterene under the name HEST® 2T-4S; polyglycerol beeswax; siliconyl beeswax; and mixtures thereof.

Other examples of waxes include polytetrafluoroethylene (PTFE), amides, bioplastics, PVP/eicosene copolymer, tricontanyl PVP, C20-40 Alkyl Stearate.

Other suitable examples of waxes or solid lipids include C20-40 di- and triglycerides, including those which contain unsaturated fatty acids, C20-40 fatty alcohols, C2-40 fatty amines and their compounds, and sterols.

Other waxes of the present invention include silicone waxes or silicone resin waxes, such as alkyl- or alkoxy-dimethicones having an alkyl or alkoxy chain ranging from 10 to 45 carbon atoms. Examples of silicone waxes are silsesquioxane resin waxes such as C30-45 alkyldimethylsilyl propylsilsesquioxane, commercially available as DOW CORNING SW-8005 C30 Resin Wax, from the company Dow Corning.

Preferred waxes having a melting point of greater than 35° C. include beeswax, commercially available from various suppliers, hydrogenated stearyl olive ester, and commercially available from the supplier Sophim under the tradename, Phytowax Olive 18 L 57, hydrogenated myristyl olive ester, and commercially available from the supplier Sophim under the tradename, Phytowax Olive 14 L 48, VP/eicosene copolymer, commercially available from the supplier ISP under the tradenames, Antaron® V 220 or Ganex® V 220F, and ditrimethyloylpropane tetrastearate, commercially available from the supplier Heterene under the tradename, HEST 2T-4S.

The wax(es) of the present invention may be chosen from soft waxes and from hard waxes. Soft waxes may be defined as those waxes which have a melting point of below about 70° C., and preferably, a melting point of below about 60° C. Hard waxes may be defined as those waxes which have a melting point of equal to or greater than about 70° C., and preferably, a melting point of equal to or greater than about 60° C.

A preferred wax for use in the powder compositions of the present invention is carnauba wax (copernicia cerifera wax), commercially available from the supplier Micro Powders, Inc. under the tradename Microcare 350.

Other preferred waxes for use in the invention are polyethylene wax, synthetic wax, polytetrafluoroethylene (PTFE), and mixtures thereof, commercially available from the supplier Micro Powders, Inc. under the tradenames Microsilk 418, Microsilk 419 and Microsilk 920.

The at least one wax of the present invention is employed in the powder composition of the present invention in an amount ranging from about 0.5% to about 20% by weight, or from about 1% to about 12% by weight, or from about 1% to about 10% by weight, or preferably from about 2% to about 10% by weight, or more preferably from about 3% to about 8% by weight, based on the total weight of the powder composition, including all ranges and subranges therebetween.

In some embodiments, the at least one wax is employed in an amount of about 12%, or of about 8%, or about 7.25%, or about 5%, or about 4%, or about 3.2%, or about 2%, by weight, based on the total weight of the powder composition.

Clay

The powder compositions of the present invention may employ at least one clay. The clay may be chosen from clays of the family of the smectites, such as laponite and montmorillonite, of the family of the kaolinites, such as kaolinite, dickite or nacrite, optionally modified clays of the family of halloysite, donbassite, antigorite, berthierine or pyrophyllite, montmorillonites, beidellite, vermiculites, talc, stevensite, hectorites, bentonites, saponites, chlorites, sepiolite and illite.

The clay or clays of the present invention can be natural or synthetic. Natural clay is a sedimentary rock in large part composed of specific minerals, silicates, generally, of aluminum. Kaolin is thus a natural clay.

Clays can also be chemically modified by various compounds, such as acrylic acids, polysaccharides (for example carboxymethylcellulose) or organic cations.

Use is preferably made, in the context of the present invention, of clays which are cosmetically compatible with and acceptable to the hair, skin and/or scalp.

Mention may be made, as natural clay, of green clays, in particular rich in illite; clays rich in montmorillonite, known under the name of fullers earth, or such as bentonites, or also white clays rich in kaolinite. Mention may in particular be made, as bentonites, of those sold under the names "Bentone 38 VCG", "Bentone Gel CAO V", "Bentone 27 V" and "Bentone Gel MIO V" by Elementis.

Montmorillonites and smectites are hydrated aluminum and/or magnesium silicates. Mention may be made, as example, of the montmorillonite sold under the name Gel White H by Rockwood Additives and of the purified smectite sold under the name Veegum Granules by Vanderbilt. Mention may also be made of the montmorillonite sold under the name Kunipia G4 by Kunimine and the sepiolite Pangel S9 sold by Tolsa.

Talcs are hydrated magnesium silicates usually comprising aluminum silicate. The crystal structure of talc consists of repeated layers of a sandwich of brucite between layers of silica.

Mention may be made, as saponite, which belongs to the family of the montmorillonites, of synthetic saponite, in particular that sold by Kunimine under the Sumecton® name. Mention may be made, as synthetic laponite, of LAPONITE® XLG, sold by Rockwood.

According to a specific embodiment of the present invention, the clay employed is chosen from kaolinites or kaolins such as those sold under the names Coslin C 100 by BASF Personal Care Ingredients or Kaolin Supreme by Imerys.

According to other embodiments, a mixture of clays can be employed in the compositions of the present invention.

The at least one clay of the present invention may be employed in the powder composition of the present invention in an amount ranging from about 1% to about 30% by weight, based on the total weight of the powder composition, including all ranges and subranges therebetween.

In preferred embodiments, the at least one clay of the present invention may be employed in the powder composition of the present invention in an amount ranging from about 1% to about 10% by weight, preferably as from about 1% to about 9% by weight, more preferably from about 2% to about 9% by weight, or even more preferably from about 5% to about 9% by weight, based on the total weight of the powder composition, including all ranges and subranges therebetween.

Non-Starch, Non-Acrylic Polymers

At least one non-starch, non-acrylic polymer may be employed in the powder compositions of the present invention. Preferably, the non-starch, non-acrylic polymer is chosen from a polyvinylpyrrolidone, a polysaccharide, and mixtures thereof.

The non-starch, non-acrylic polymer may function as a thickening or viscosity agent in the compositions of the present invention.

Suitable examples of the non-starch, non-acrylic polymer of the present invention include polysaccharides chosen from xanthan gum, cellulose gum, guar gum, algin, chitosan, hydroxyethylcellulose, hydroxypropylcellulose, cetyl hydroxyethylcellulose, and mixtures thereof.

Preferred non-starch, non-acrylic polymer of the present invention are selected from xanthan gum, cellulose gum, polyvinylpyrrolidone, and mixtures thereof.

The at least one non-starch, non-acrylic polymer may also be chosen from cationic polymers such as polyquaternium compounds.

In one embodiment, the at least one non-starch, non-acrylic polymer is polyquaternium-5.

The at least one non-starch, non-acrylic polymer of the present invention may be employed in the powder composition of the present invention in an amount ranging from about 0.1% to about 10% by weight, preferably from about 0.5% to about 8% by weight, more preferably from about 0.5% to about 5% by weight, and even more preferably from about 2% to about 5% by weight, based on the total weight of the powder composition, including all ranges and subranges therebetween.

In some embodiments, when a cationic polymer is employed, the amount of the cationic polymer in the powder composition of the invention is not more than about 1% by weight, based on the total weight of the composition.

Aqueous Composition

The aqueous composition of the present invention comprises a cosmetically acceptable solvent selected from water and a water/organic solvent mixture. A water that is suitable for use in the invention may be a floral water such as cornflower water and/or a mineral water such as Vittel water, Lucas water or La Roche Posay water and/or a spring water and/or tap water and/or well water.

The aqueous composition may also comprise water-miscible organic solvents (at room temperature: 25° C.), for instance monoalcohols containing from 2 to 6 carbon atoms, such as ethanol or isopropanol; polyols especially containing from 2 to 20 carbon atoms, preferably containing from 2 to 10 carbon atoms and preferentially containing from 2 to 6 carbon atoms, such as glycerol, propylene glycol, butylene glycol, pentylene glycol, hexylene glycol, dipropylene glycol or diethylene glycol; glycol ethers (especially containing from 3 to 16 carbon atoms) such as mono-, di- or tripropylene glycol (C1-C4)alkyl ethers, mono-, di- or triethylene glycol (C1-C4)alkyl ethers, and mixtures thereof.

The aqueous composition may also comprise stabilizers, for example sodium chloride, magnesium dichloride or magnesium sulfate.

The aqueous composition may also comprise any water-soluble or water-dispersible compound that is compatible with an aqueous phase, such as the above-described acrylic polymers, non-starch, non-acrylic polymers, starch, silica particles, liquid fatty substances, wax, and mixtures thereof.

In some embodiments, the aqueous composition comprises 100% water by weight.

When the aqueous composition comprises 100% water, the water may be provided by the end user in the form of tap water or drinking water.

In particular, the aqueous composition of the invention may comprise water in a content ranging from about 45% to about 100% by weight, or from about 50% to about 90% by weight, or from about 50% to 80% by weight, based on the total weight of the composition, including all ranges and subranges therebetween.

The aqueous composition of the present invention may be in the form of a liquid, a lotion, or a cream; it can also be an emulsion, preferably, an oil-in-water emulsion.

Chelant Compounds

At least one a chelant compound is employed in the powder and/or aqueous compositions of the present invention. The chelant compounds of the present invention are chosen from ethylene diamine tetraacetic acid (EDTA) and its salts; N-(hydroxyethyl) ethylene diamine triacetic acid and its salts; aminotrimethylene phosphonic acid and its salts; diethylenetriamine-pentaacetatic acid and its salts; lauroyl ethylene diamine triacetic acid and its salts; nitrilotriacetic acid and its salts; iminodisuccinic acid and its salts; tartaric acid and its salts; citric acid and its salts; N-2-hydroxyethyliminodiacetic acid and its salts; ethyleneglycol-bis(beta-amino ethyl ether)-N,N-tetraacetic acid; and pentasodium aminotrimethylene phosphonate. The salts may be chosen from salts with organic or inorganic cations. In one embodiment, the inorganic cation is chosen from potassium, sodium or lithium.

In a further preferred embodiment, a salt of EDTA, such as sodium, lithium, potassium or guanidine EDTA, is the complexing agent.

The at least one chelating compound may also be combined with at least one sequestering agent.

The at least one chelant compound may be present in the powder or aqueous compositions of the invention in an amount of from about 0.5% to about 5% by weight, preferably from about 0.8% to about 4% by weight, more preferably from about 0.8% to about 3% by weight, and more preferably from about 1% to about 2.5% by weight, such as at about 1%, or about 1.5%, or about 2%, or about 2.5%, based on the total weight of the composition.

Surfactants

The powder composition and aqueous composition according to the invention may further comprise at least one surfactant selected from anionic surfactants, nonionic surfactants, amphoteric or zwitterionic surfactants and cationic surfactants, and mixtures thereof.

Anionic Surfactants

The term "anionic surfactant" is understood to mean a surfactant comprising, as ionic or ionizable groups, only anionic groups. These anionic groups are preferably chosen from the following groups: CO2H, CO2-, SO3H, SO3-, OSO3H, OSO3-, H2PO3, —HPO3-, —PO32-, —H2PO2, =HPO2, —HPO2-, =PO2-, =POH and =PO—.

Mention may be made, among the anionic surfactants capable of being used in the composition according to the invention, of alkyl sulfates, alkyl ether sulfates, alkylamido ether sulfates, alkylaryl polyether sulfates, monoglyceride sulfates, alkylsulfonates, alkylamidesulfonates, alkylarylsulfonates, α-olefinsulfonates, paraffinsulfonates, alkyl sulfosuccinates, alkyl ether sulfosuccinates, alkylamide sulfosuccinates, alkyl sulfoacetates, acyl sarcosinates, acyl glutamates, alykyl ether carboxylates, alkyl sulfosuccinamates, acyl isethionates and N-acyl taurates; monoalkyl esters of polyglycoside-polycarboxylic acids, acyl lactylates, salts of D-galactosideuronic acids, salts of alkyl ether carboxylic acids, salts of alkylaryl ether carboxylic acids, salts of alkylamido ether carboxylic acids; and the corresponding non-salified forms of all these compounds; the alkyl and acyl groups of all these compounds comprising from 6 to 24 carbon atoms and the aryl group denoting a phenyl group.

These compounds can be oxyethylenated and then preferably comprise from 1 to 50 ethylene oxide units and better still from 1 to 10 ethylene oxide units.

The salts of C6-C24 alkyl monoesters of polyglycoside-polycarboxylic acids can be chosen from C6-C24 alkyl polyglycoside-citrates, C6-C24 alkyl polyglycoside-tartrates and C6-C24 alkyl polyglycoside-sulfosuccinates.

The acyl lactylates preferably have an acyl group comprising from 8 to 20 carbon atoms.

When the anionic surfactant is in the salt form, it can be chosen from the alkali metal salts, such as the sodium salt or potassium salt, the ammonium salt, the amine salts and in particular the aminoalcohol salts, or the alkaline earth metal salts, such as the magnesium salt.

Use is preferably made of alkali metal or alkaline earth metal salts and in particular of sodium or magnesium salts.

The preferred anionic surfactants are chosen from (C6-24)alkyl sulfates, (C6-24)alkyl ether sulfates, acyl glutamates and (C6-C24)alkyl ether carboxylates, in particular in the form of alkali metal, ammonium, aminoalcohol or alkaline earth metal salts, or a mixture of these compounds.

In particular, use is preferably made of (C12-20)alkyl sulfates, (C12-20)alkyl ether sulfates comprising from 2 to 20 ethylene oxide units, acyl glutamates or (C12-C20)alkyl ether carboxylates, in particular in the form of alkali metal, ammonium, aminoalcohol and alkaline earth metal salts, or a mixture of these compounds.

Nonionic Surfactants

The at least one non-ionic surfactants may be chosen, for example, from polyethoxylated and/or polypropoxylated alkyl phenols, alpha-diols and alcohols, comprising fatty chains comprising, for example, from 8 to 18 carbon atoms, and the number of ethylene oxide and/or propylene oxide groups may range from 2 to 50. The at least one non-ionic surfactant may be chosen, for example, from copolymers of ethylene oxide and of propylene oxide, condensates of ethylene oxide and/or of propylene oxide with fatty alcohols; polyethoxylated fatty amides comprising, for example, from 2 to 30 moles of ethylene oxide, polyglycerolated fatty amides comprising on average 1 to 5, and, for example, 1.5 to 4, glycerol groups; polyethoxylated fatty amines comprising, for example, from 2 to 30 moles of ethylene oxide; oxyethylenated fatty acid esters of sorbitan comprising, for example, from 2 to 30 moles of ethylene oxide; fatty acid esters of sucrose, fatty acid esters of polyethylene glycol, alkylpolyglycosides, N-alkylglucamine derivatives, and amine oxides such as (C10-C14)alkyl amine oxides and N-acylaminopropylmorpholine oxides.

Amphoteric or Zwitterionic Surfactants

The amphoteric or zwitterionic surfactants can in particular be derivatives of optionally quaternized secondary or tertiary aliphatic amines comprising at least one anionic group, such as, for example, a carboxylate, sulfonate, sulfate, phosphate or phosphonate group, and in which the aliphatic group or at least one of the aliphatic groups is a linear or branched chain comprising from 8 to 22 carbon atoms.

Mention may in particular be made of (C8-C20)alkyl betaines, sulfobetaines, (C8-C20)alkylamido(C1-C6)alkyl betaines, such as cocoamidopropyl betaine, or (C8-C20) alkylamido(C1-C6)alkyl sulfobetaines.

Mention may also be made of optionally quaternized secondary or tertiary aliphatic amines such as disodium cocoamphodiacetate, disodium lauroamphodiacetate, disodium caprylamphodiacetate, disodium caprylamphodiacetate, disodium cocoamphodi-propionate, disodium lauroamphodipropionate, disodium caprylamphodipropio-nate, disodium caprylamphodipropionate, lauroamphodipropionic acid and co-coampho¬ idipropionic acid.

Mention may be made, by way of example, of the cocoamphodiacetate sold by Rhodia under the trade name Miranol® C2M Concentrate.

Mention may also be made of the compound under the name sodium diethylaminopropyl cocoaspartamide and sold by Chimex under the name Chimexane HB.

Preferably, the amphoteric or zwitterionic surfactants are chosen from (C8-C20)alkyl betaines, (C8-C20)alkylamido (C1-C6)alkyl betaines and (C8-C20)alkylamphodiacetates, and also the sodium salt of diethylaminopropyl laurylaminosuccinamate, and their mixtures.

Preferably, the amphoteric or zwitterionic surfactants are chosen, alone or as a mixture, from cocoylamidopropyl betaine, cocoyl betaine and cocoamphodiacetate.

Cationic Surfactants

The at least one cationic surfactant may be chosen, for example, from: salts of optionally polyoxyalkylenated primary, secondary and tertiary fatty amines; quaternary ammonium salts such as tetra alkyl ammonium, alkylamidoalkyltrialkyl ammonium, trialkylbenzyl ammonium, trialkylhydroxyalkyl ammonium and alkylpyridinium chlorides and bromides; imidazoline derivatives; and cationic amine oxides.

The at least one surfactant may be present in the powder composition and/or the aqueous composition in an amount ranging from about 0.01 to about 40%, such as from 0.05 to 30% by weight, or from about 0.1 to about 30% by weight, or from about 1 to about 20% by weight, based on the total weight of the compositions.

Auxiliary Ingredients

The powder compositions and aqueous compositions according to the invention may also comprise any auxiliary ingredient usually used in the field under consideration, selected, for example, from organic amines, emulsifying agents, fillers, pigments, conditioning agents, moisturizing agents, additional viscosity or thickening agents, shine agents, sequestering agents, fragrances, preservatives, pH modifiers/neutralizing agents, stabilizers, and mixtures thereof.

It is a matter of routine operations for a person skilled in the art to adjust the nature and amount of the additives present in the compositions in accordance with the invention such that the desired cosmetic properties and stability properties thereof are not thereby affected.

If present in the powder or aqueous composition, these auxiliary ingredients may constitute from about 0.5% to about 30%, typically from about 1%% to about 15% and more typically, from about 1% to about 10% by weight, based on the total weight of the composition.

The present invention relates to a powder composition comprising an alkaline material comprising hydroxide-containing compounds, at least two carbonate compounds, a sulfur-containing compound, starch, silica material, liquid fatty substance, and, an acrylic polymer. Said composition can additionally contain a chelant compound, a wax, a non-starch, non-acrylic polymer, clay, surfactant, and an auxiliary ingredient.

In certain embodiments, the powder composition is essentially free of water.

The powder composition is capable of being mixed with an aqueous composition comprising a cosmetically acceptable solvent selected from water and a water/organic solvent mixture in order to form a ready to use composition.

The term "mixed" and all variations of this term as used herein refers to contacting or combining or reconstituting or dissolving or dispersing or blending or shaking the powder composition with the aqueous composition. It can also mean introducing the powder composition to the aqueous composition. It may also mean placing the powder composition in the same vessel or container as the aqueous composition.

The step of contacting the powder composition with the aqueous composition can be conducted in any vessel suitable for holding the resulting ready to use composition. The step of contacting the powder composition with the aqueous composition can be conducted in situ, that is, on the hair or skin that is intended to be treated.

The powder composition of the present invention may be mixed with varying amounts of the aqueous composition of the present invention to obtain a ready to use composition with properties suitable for a particular use.

The term "ready to use composition" as used herein refers to the composition that is to be applied onto hair and comprises the powder composition and the aqueous composition of the invention. Generally, the ready to use composition is to be prepared by the consumer on the day that the depilation or hair removal is to be done. It can be applied onto hair immediately after it is prepared. There could also be a certain period of time before the ready to use composition is applied onto the hair or the skin with hair from the time of preparation of said composition, such as from between about 2 minutes to about 60 minutes, or such as from between about 2 minutes to about 30 minutes.

In some embodiments, the aqueous composition comprises 100% by weight of water and may be provided by the manufacturer of the powder composition or consumer or end-user such as a cosmetologist.

In certain embodiments, the resulting ready to use composition is comprised of the powder composition and the aqueous composition in a weight ratio of from about 1:3 to about 1:4 up to 1:10.

In other embodiments, the weight ratio of the powder composition to the aqueous composition in the ready to use composition is about 1:3.

In yet other embodiments, the weight ratio of the powder composition to the aqueous composition in the ready to use composition is about 1:4.

In preferred embodiments, the ready to use composition has a viscosity ranging from about 30 uD to about 100 uD, preferably from about 50 uD to about 90 uD, or from about 60 uD to about 80 uD, or from about 70 uD to about 90 uD.

In other preferred embodiments, the ready to use composition has a pH of greater than 7, and ranges from about 9 to about 14, such as from about 10 to about 14, preferably, from about 11 to about 13, or more preferably from about 12 to about 14.

In certain preferred embodiments, the ready to use composition has a viscosity ranging from about 70 uD to about 90 uD and a pH ranging from about 12 to about 14.

All numbers expressing pH values are to be understood as being modified in all instances by the term "about" which encompasses up to +/−3%. For example, a pH value of about 7.0 refers to 7+/−0.21.

In preferred embodiments, the ready to use composition is a depilatory composition.

The powder composition of the present invention is stable such that the activity or efficacy of the alkaline material and the sulfur-containing compound is preserved until the powder composition is ready to be used or mixed with the aqueous composition of the invention.

In addition, the powder composition of the present invention is stable over time due to minimal moisture content; it can be stored for several months without modification.

The powder composition of the present invention was also surprisingly and unexpectedly discovered to be a free flowing powder that is easy to handle, is easily pourable, has non-sticky and non-clinging properties, and does not exhibit visible clumping.

The powder composition remains free flowing after packaging and storage.

The powder composition may be packaged in any suitable container. It may also be packaged as one unit or as part of a multi-compartment kit which additionally contains a second unit containing an aqueous composition comprising water or a water/organic solvent mixture.

Process of Making the Powder Composition

The powder composition of the invention may be prepared according to the general procedure below:

In a first container, a starch material is combined or mixed with a liquid fatty substance such as an oil and mixed at speed of at least about 200 RPM using a Rayneri mixer (or other suitable alternative mixer) for at least about 2 minutes or until a white liquid mixture is obtained.

A silica material (e.g., silica silylate and/or hydrated silica and/or hydrophobic silica aerogel material) is then added slowly to the starch/oil mixture and mixing is continued until the mixture turns into a powder called the powdered oil system.

In a second container, an acrylic polymer, wax, chelant, alkaline material comprising at a hydroxide-containing compound, sulfur-containing compound, and optional ingredients are mixed at speed of at least about 200 RPM using a Rayneri mixer (or other suitable alternative mixer) for at least about 20 minutes.

The powdered oil system is then slowly added to the ingredients in the second container and mixing is continued for about 10 minutes.

Method of Depilating Hair

The invention also concerns a method of depilating hair, the method comprising the steps of: 1) mixing the powder composition with the aqueous composition in a particular weight ratio, such as from about 1:3 to about 1:10, and preferably, from about 1:3 to about 1:4, in order to form a ready to use composition for relaxing or straightening the hair, wherein the pH of the ready to use composition ranges from about 9 to about 14; and wherein the viscosity of the ready to use composition is from about 30 uD to about 100 uD; and 2) contacting the hair with the ready to use composition for a sufficient period of time to achieve a desired depilatory effect.

The ready to use compositions of the present invention is applied to the hair in sufficient amount as to desirably or effectively remove or degrade hair.

In certain embodiments, the ready to use composition formed from mixing the powder composition in the aqueous composition of the present invention is left to stand on the hair for a period of time ranging from about 5 to 60 minutes, and preferably, from 5 to 30 minutes, after which, the depilated hair is rinsed or wiped off from the skin.

It has been surprisingly and unexpectedly discovered that the combination of an alkaline material comprising hydroxide-containing compounds, at least two carbonate compounds, a sulfur-containing compound, starch, silica material, liquid fatty substance, acrylic polymer, and chelant compound forms a powder, which, when combined with the aqueous composition of the present invention, produces a final mixture or a ready to use composition with a non-drip consistency that is still easy to spread on keratin substrates, such as hair or skin with hair. This consistency is also characterized in terms of viscosity which was found to range from about 30 uD to about 100 uD.

It has surprisingly and unexpectedly discovered that the application of the ready to use composition onto the fibers results in satisfactory removal or depilation of hair. The removal or depilation of hair may be evaluated by visually assessments.

Notwithstanding that the numerical ranges and parameters setting forth the broad scope of the invention are approximations, the numerical values set forth in the specific examples are reported as precisely as possible. Any numerical value, however, inherently contain certain errors necessarily resulting from the standard deviation found in their respective measurements. The following examples are intended to illustrate the invention without limiting the scope as a result.

EXAMPLES

The following Examples are intended to be non-restrictive and explanatory only, with the scope of the invention being defined by the claims.

The ingredient amounts in the compositions/formulas described below are expressed in % by weight, based on the total weight of the composition/formula.

Example 1

Inventive Compositions

TABLE 1

Inventive powder compositions (formulas A to C) and comparative composition

| Ingredients | Formula A* | Formula B* | Formula C* | Comparative composition |
|---|---|---|---|---|
| CALCIUM CARBONATE | 27.5 | 27.5 | 27.5 | 27.5 |
| CALCIUM HYDROXIDE | 6.0 | 6.0 | 6.0 | 6.00 |
| GUANIDINE CARBONATE | 1.5 | 1.5 | 1.5 | 1.5 |
| CALCIUM THIOGLYCOLATE | 10.0 | 10.0 | 10.0 | 10.0 |
| Sodium Lauryl Sulfate | 3.0 | 5.0 | 2.0 | — |
| EDTA | 0.8 | 0.8 | 1.0 | — |
| Kaolin | 5.0 | 5.0 | 9.0 | — |
| MINERAL OIL | 26.07 | 20.0 | 6.0 | — |
| Corn Starch | 3.05 | 3.05 | 10.0 | 54.0 |
| Titanium Dioxide | 2.0 | 2.0 | 1.0 | — |
| Sodium Polyacrylate (Cognis, 90% active) | 2.75 | 3.0 | 8.0 | — |
| Polyethylene Wax | 1.0 | 2.25 | 12.0 | — |
| Polyethylene & Synthetic Wax & polytetrafluoroethylene (PTFE) (Microsilk 418, Micro Powders) | 3.15 | 5.0 | — | — |
| Capina Wax | 1.0 | 1.55 | — | — |
| OLETH-30 | 1.0 | 1.0 | — | — |
| SILICA SILYLATE (VM-2270, Dow Corning, 98% active) | 0.68 | 0.68 | 1.0 | — |

TABLE 1-continued

Inventive powder compositions (formulas A to C) and comparative composition

| Ingredients | Formula A* | Formula B* | Formula C* | Comparative composition |
|---|---|---|---|---|
| ACRYLATES/C10-30 ALKYL ACRYLATE CROSSPOLYMER (Carbopol ® ETD 2020 Polymer, Lubrizol) | 1.0 | 1.17 | 1.5 | — |
| Glyceryl Dibehenate and Tribehenin and Glyceryl Behenate | — | — | 1.0 | — |
| Non-starch, non-acrylic polymer(s) | 4.5 | 4.5 | 2.5 | — |
| Fragrance and polysorbate-21 | | | | 1.0 |
| Total | 100.0 | 100.0 | 100.0 | 100.0 |
| Mix Ratio (formula to water) | 1:3 | 1:3 | 1:3 | 1:3 |
| Description | Mix was smooth and creamy | Mix was smooth and creamy | Mix was smooth and creamy | Mix was not creamy |
| Mix pH | 12.15 | 12.36 | 13.23 | 12.85 |
| Mix viscosity | 79.12 uD | 83.62 uD | 76.84 uD | 15.3 uD |

*The formulas were in powder form.

The inventive powder compositions in Table 1 were prepared according to the protocol as follows:
1. The starch was added into a 1 kg beaker.
2. Mineral Oil was added to the beaker.
3. The ingredients in the beaker were mixed on the Rayneri at 200-300 RPM for 2 minutes resulting in a white liquid mixture.
4. The silica material was added slowly and carefully to the mixture and the mixture began to turn into a powder (powdered oil system).
5. The bottom of the beaker was scraped to ensure that all the oil was absorbed.
6. Mixing speed was increased to 400-500 RPM and mixing was continued for 5 minutes.
7. The rest of the ingredients were combined in a separate beaker and mixed with the Rayneri at 200-300 RPM for 20 minutes.
8. The powdered oil system (mineral oil, starch and silica material) was slowly added to the rest of the ingredients.
9. The final mixture was mixed for 10 minutes.

The inventive powder compositions in Table 1 were observed to be free flowing and did not exhibit visible agglomeration/aggregation or clumping. The powder particles were not sticking to each other and the inventive powder compositions were easily pourable and easily mixed with water or with an aqueous composition.

Each of the compositions above was mixed with a solvent (water) according to the ratios indicated in the bottom of the table in order to form ready to use compositions.

When the comparative formula was mixed with water in a 1:3 ratio, the resulting composition (ready to use comparative composition) was not creamy, that is, it was watery or runny, not easy to apply on skin and dried out fast (in about 7 minutes) on the skin surface upon application.

In contrast, the ready to use compositions prepared from the powder composition of the invention were thick, creamy and smooth (not runny or watery), easy to apply onto the skin, and did not run off the skin surface.

The viscosities and the pH of the ready to use compositions ("mix pH" and "mix viscosity") of the invention were then measured and are presented in Table 1 as well. The measured viscosities are generally associated with a creamy and smooth texture as indicated in the table. The ready to use compositions also had non-drip consistencies, i.e, they were not runny or watery.

Viscosity was measured using the Mettler RM 180 Rheomat spindle #3 at 25° C. (uD=Units of Deflection).

After the ready to use compositions of the invention were removed or rinsed off from the skin, the skin was not dry, felt smooth and soft, and caused less skin irritation as compared to a conventional/traditional depilatory product.

Example 2

Viscosity and pH Studies Over Time

The viscosity and pH of the ready to use composition which was prepared by mixing the inventive powder composition (Formula B) with an aqueous composition (100% by weight of water) were measured at room temperature over various time points at room temperature in order to determine whether the viscosity and pH of the ready to use composition changed over a period of 60 minutes with constant mixing using a Rayneri mixer.

TABLE 2

Viscosity and pH study

| Time* (min) | Viscosity (uD) | pH |
|---|---|---|
| 0 | 83.62 | 12.36 |
| 5 | 83.56 | 12.39 |
| 10 | 83.48 | 12.36 |
| 15 | 83.69 | 12.15 |
| 20 | 83.75 | 12.35 |
| 25 | 83.97 | 12.59 |
| 30 | 84.10 | 12.35 |
| 35 | 83.56 | 12.35 |
| 40 | 83.59 | 12.35 |
| 45 | 85.15 | 12.37 |
| 50 | 85.17 | 12.38 |
| 55 | 85.00 | 12.35 |
| 60 | 85.96 | 12.35 |
| percent change** | 2.8% | |

*time from mixing the inventive composition and the aqueous composition of the invention
**difference between T(0 min) and T(60 min)/T(0 min)

The results in the table above show that the changes in viscosity and pH over time of the ready to use composition of the invention was very small. This shows that the powder composition of the invention can be easily combined with an aqueous composition in order to prepare a ready to use composition having a desirable consistency and texture and a pH necessary for achieving effective removal of hair.

Example 3

Stability of Inventive Powder Compositions

The inventive powder compositions were shown to be stable up to 8 weeks in a controlled chamber at various temperatures at 5° C., 25° C., 37° C., and 45° C. as well as 10 days in a Freeze/Thaw cycle where the pH and viscosity had small fluctuations and there was no phase separation.

No clumping or agglomeration/aggregation of the powder compositions was visually observed.

It is to be understood that the foregoing describes preferred embodiments of the invention and that modifications may be made therein without departing from the spirit or scope of the invention as set forth in the claims.

What is claimed is:

1. A powder composition comprising:
   (a) from about 1% to about 30% by weight of at least one hydroxide-containing compound selected from the group consisting of alkali metal hydroxides, alkaline-earth metal hydroxides, transition metal hydroxides, and mixtures thereof;
   (b) from about 20% to about 40% by weight of at least two carbonate compounds selected from the group consisting of calcium carbonate, lithium carbonate, sodium carbonate, potassium carbonate, guanidine carbonate, and mixtures thereof;
   (c) from about 1% to about 25% by weight of at least one starch material;
   (d) from about 0.1% to about 20% by weight of at least one silica material;
   (e) from about 5% to about 50% by weight of at least one liquid fatty substance selected from the group consisting of $C_6$-$C_{16}$ alkanes, non-silicone oils of plant, mineral or synthetic origin, liquid fatty alcohols, liquid fatty acids and liquid esters of a fatty acid and/or of a fatty alcohol, and mixtures thereof;
   (f) from about 0.5% to about 15% by weight of at least one acrylic polymer;
   (g) from about 5% to about 20% by weight of at least one sulfur-containing compound selected from the group consisting of calcium thioglycolate, potassium thioglycolate, sodium thioglycolate, ammonium thioglycolate, strontium thioglycolate, magnesium thioglycolate, diammonium dithiodiglycolate, 2-methoxyethyl thioglycolate, 2-ethoxyethyl thioglycolate, 2-ethoxypropyl thioglycolate, methyl thioglycolate, ethyl thioglycolate, butyl thioglycolate, isooctyl thioglycolate, isopropyl thioglycolate, guanidine thioglycolate, glyceryl monothioglycolate, monoethanolamine thioglycolate, monoethanolamine thioglycolic acid, diammoniumdithiodiglycolate, dithioerythritol, thioglycerol, thioglycol, thioxanthine, thiosalicylic acid, N-acetyl-L-cysteine, lipoic acid, sodium dihydrolipoate 6,8-dithioocatanoate, sodium 6,8-diothioocatanoate, a hydrogen sulphide salt, thioglycolic acid, 2-mercaptopropionic acid, 3-mercaptopropionic acid, thiomalic acid, ammonium thiolactate, monoethanolamine thiolactate, thioglycolamide, homocysteine, cysteine, glutathione, dithiothreitol, dihydrolipoic acid, 1,3-dithiopropanol, thioglycolamide, glycerylmonothioglycolate, thioglycolhydrazine, keratinase, cysteamine, and mixtures thereof; and
   (h) from about 0.5% to about 5% by weight of at least one chelant compound;
   all weights above being based on the total weight of the powder composition.

2. The powder composition of claim 1, wherein the hydroxide-containing compound is selected from the group consisting of sodium hydroxide, potassium hydroxide, lithium hydroxide, calcium hydroxide, and mixtures thereof.

3. The powder composition of claim 1, wherein the hydroxide-containing compound is calcium hydroxide and the two carbonate compounds are calcium carbonate and guanidine carbonate.

4. The powder composition of claim 3, wherein calcium carbonate is present in an amount of from about 25% to about 30% by weight, based on the total weight of the powder composition.

5. The powder composition of claim 4, wherein guanidine carbonate is present in an amount of from about 1% to about 2% by weight, based on the total weight of the powder composition.

6. The powder composition of claim 5, wherein the starch is selected from the group consisting of: (i) starches derived from a plant source selected from the group consisting of corn, potato, sweet potato, pea, barley, wheat, rice, oat, sago, tapioca and sorghum; (ii) hydrolyzed starches selected from the group consisting of dextrin and maltodextrin; and (iii) modified starches; and mixtures thereof.

7. The powder composition of claim 6, wherein the starch is selected from the group consisting of corn starch, potato starch, dextrin, maltodextrin, and mixtures thereof.

8. The powder composition of claim 7, wherein the starch is present in an amount of from about 3% to about 10% by weight, based on the total weight of the powder composition.

9. The powder composition of claim 7, wherein the silica material comprises silica particles selected from the group consisting of hydrated silica, hydrophobic silica aerogel particle, and mixtures thereof.

10. The powder composition of claim 9, wherein the silica material is present in an amount of from about 0.1% to about 5% by weight, based on the total weight of the powder composition.

11. The powder composition of claim 9, wherein the fatty substance is a non-silicon oil of plant, mineral, or synthetic origin.

12. The powder composition of claim 11, wherein the fatty substance is present in an amount of from about 5% to about 40% by weight, based on the total weight of the powder composition.

13. The powder composition of claim 12, wherein the acrylic polymer is a crosslinked acrylic polymer and is present in an amount of from about 1% to about 10% by weight, based on the total weight of the powder composition.

14. The powder composition of claim 13, wherein the crosslinked acrylic polymer is selected from sodium polyacrylate, carbomer, acrylates C10-30 alkyl acrylate crosspolymer, and mixtures thereof.

15. The powder composition of claim 1, wherein the sulfur-containing compound is selected from the group consisting of calcium thioglycolate, potassium thioglycolate, ammonium thioglycolate, and mixtures thereof.

16. The powder composition of claim 1, wherein the chelant compound is selected from the group consisting of ethylenediaminetetraacetic acid (EDTA), and its salts; N-(hydroxyethyl) ethylene diamine triacetic acid and its salts; aminotrimethylene phosphonic acid and its salts;

diethylenetriamine-pentaacetatic acid and its salts; lauroyl ethylene diamine triacetic acid and its salts; nitrilotriacetic acid and its salts; iminodisuccinic acid and its salts; tartaric acid and its salts; citric acid and its salts; N-2-hydroxyethyliminodiacetic acid and its salts; ethyleneglycol-bis(beta-amino ethyl ether)-N,N-tetraacetic acid; and pentasodium aminotrimethylene phosphonate, and mixtures thereof.

17. The powder composition of claim 16, further comprising from about 1% to about 10% by weight of at least one wax.

18. The powder composition of claim 1, further comprising at least one non-starch, non-acrylic polymer selected from the group consisting of a polyvinylpyrrolidone, a polysaccharide, and mixtures thereof.

19. The powder composition of claim 18, wherein the non-starch, non-acrylic polymer is selected from the group consisting of xanthan gum, cellulose gum, guar gum, algin, chitosan, hydroxyethylcellulose, hydroxypropylcellulose, cetyl hydroxyethylcellulose, polyvinylpyrrolidone and mixtures thereof.

20. The powder composition of claim 19, wherein the non-starch polymer is present in an amount of from about 0.1% to about 10% by weight, based on the total weight of the powder composition.

21. The powder composition of claim 1, wherein the composition further comprises at least one clay selected from the group consisting of kaolin, bentonites, montmorillonites, hectorites, beidellites, saponites, laponite, dickite, nacrite, optionally modified clays of the family of halloysite, vermiculite, talc, stevensite, chlorite, sepiolite, and mixtures thereof.

22. The powder composition of claim 21, wherein the clay is present in an amount of from about 1% to about 10% by weight, based on the total weight of the powder composition.

23. The powder composition of claim 16, wherein the powder composition is essentially free of water.

24. The powder composition of claim 1, wherein the powder composition is capable of being mixed with an aqueous composition comprising a cosmetically acceptable solvent selected from water and a water/organic solvent mixture in order to form a ready to use composition.

25. The powder composition of claim 23, wherein the powder composition is capable of being mixed with an aqueous composition comprising a cosmetically acceptable solvent selected from the group consisting of water and a water/organic solvent mixture in order to form a ready to use composition in a weight ratio of from about 1:3 to about 1:10.

26. The powder composition of claim 25, wherein the ready to use composition has a pH of from about 9 to about 14.

27. A process of depilating or removing hair, comprising contacting hair with the ready to use composition of claim 26.

28. The powder composition of claim 23, wherein the powder composition and/or the aqueous composition further comprises at least one surfactant selected from the group consisting of anionic surfactants, nonionic surfactants, amphoteric surfactants and mixtures thereof.

29. The powder composition and/or the aqueous composition of claim 25, further comprising at least one auxiliary ingredient selected from the group consisting of organic amines, emulsifying agents, fillers, pigments, conditioning agents, moisturizing agents, additional viscosity or thickening agents, shine agents, sequestering agents, fragrances, preservatives, pH modifiers/neutralizing agents, stabilizers, and mixtures thereof.

30. A powder composition comprising:
(a) from about 3% to about 10% by weight of calcium hydroxide;
(b) from about 25% to 35% by weight of calcium carbonate and guanidine carbonate;
(c) from about 1% to about 15% by weight of at least one starch selected from the group consisting of: (i) starches derived from a plant source selected from corn, potato, sweet potato, pea, barley, wheat, rice, oat, sago, tapioca and sorghum; (ii) hydrolyzed starches selected from dextrin and maltodextrin; (iii) modified starches; and mixtures thereof;
(d) from about 0.5% to about 3% by weight of silica particles selected from the group consisting of hydrated silica particles, hydrophobic silica aerogel particles, and mixtures thereof;
(e) from about 20% to about 30% by weight of mineral oil;
(f) from about 1% to about 10% by weight of at least one acrylic polymer selected from the group consisting of sodium polyacrylate, carbomer, acrylates C10-30 alkyl acrylate cross polymer, and mixtures thereof; and
(g) from about 8% to about 15% by weight of at least one sulfur-containing compound selected from the group consisting of calcium thioglycolate, potassium thioglycolate, ammonium thioglycolate, and mixtures thereof;
(h) from about 0.5% to about 5% by weight of at least one chelant compound selected from the group consisting of ethylenediaminetetraacetic acid (EDTA), its salts, and mixtures thereof;
(i) from about 1% to about 10% by weight of at least one wax;
(j) from about 0.5% to about 5% by weight of non-starch, non-acrylic polymer selected from the group consisting of a polyvinylpyrrolidone, a polysaccharide, and mixtures thereof;
(k) from about 1% to about 10% by weight of at least one clay; and
all weights above being are based on the total weight of the powder composition.

31. A method for depilating hair, the method comprising:
(a) mixing a powder composition of claim 1 with an aqueous composition in a weight ratio of about 1:3 to about 1:10,
(b) forming a ready-to-use composition for relaxing or straightening the hair; and
(c) contacting the hair with the ready-to-use composition for a sufficient period of time to achieve a desired relaxation or straightening.

32. A multi-compartment kit for relaxing or straightening hair comprising at least two compartments, wherein a first compartment contains a powder composition of claim 1.

* * * * *